United States Patent
Otvos et al.

(10) Patent No.: US 9,483,612 B2
(45) Date of Patent: Nov. 1, 2016

(54) CHD RISK STRATIFICATION EVALUATIONS FOR SUBJECTS WITH HIGH LEVELS OF LARGE HDL-P

(71) Applicant: LipoScience, Inc., Raleigh, NC (US)

(72) Inventors: James D. Otvos, Cary, NC (US); Irina Y. Shalaurova, Cary, NC (US)

(73) Assignee: LIPOSCIENCE, INC., Raleigh, NC (US)

( * ) Notice: Subject to any disclaimer, the term of this patent is extended or adjusted under 35 U.S.C. 154(b) by 77 days.

(21) Appl. No.: 13/871,873

(22) Filed: Apr. 26, 2013

(65) Prior Publication Data

US 2013/0289885 A1 Oct. 31, 2013

Related U.S. Application Data

(60) Provisional application No. 61/639,508, filed on Apr. 27, 2012.

(51) Int. Cl.
| | | |
|---|---|---|
| *G01N 33/48* | (2006.01) | |
| *G01N 33/50* | (2006.01) | |
| *G06F 19/00* | (2011.01) | |
| *G01N 33/92* | (2006.01) | |

(52) U.S. Cl.
CPC .............. *G06F 19/30* (2013.01); *G01N 33/92* (2013.01); *G06F 19/34* (2013.01); *G06F 19/3437* (2013.01); *G06F 19/3443* (2013.01)

(58) Field of Classification Search
None
See application file for complete search history.

(56) References Cited

U.S. PATENT DOCUMENTS

| | | |
|---|---|---|
| 4,933,844 A | 6/1990 | Otvos |
| 6,617,167 B2 | 9/2003 | Otvos et al. |
| 7,250,304 B2 | 7/2007 | Fogelman et al. |
| 7,491,543 B2 | 2/2009 | Barzilai |
| 7,723,045 B2 | 5/2010 | Fogelman et al. |
| 7,771,954 B2 | 8/2010 | Hazen et al. |
| 8,013,602 B2 | 9/2011 | Otvos et al. |
| 8,386,187 B2 | 2/2013 | Otvos |
| 2004/0229275 A1* | 11/2004 | Hayden et al. .............. 435/6 |
| 2005/0244892 A1 | 11/2005 | Lazar et al. |
| 2007/0264677 A1 | 11/2007 | Otvos |
| 2010/0285517 A1 | 11/2010 | Hazen et al. |
| 2011/0124031 A1 | 5/2011 | Hazen et al. |
| 2011/0201947 A1 | 8/2011 | Hazen et al. |

FOREIGN PATENT DOCUMENTS

| | | |
|---|---|---|
| WO | WO 00/51054 * | 8/2000 |
| WO | WO 2011/153271 A1 | 12/2011 |
| WO | WO 2012/045773 A1 | 4/2012 |

OTHER PUBLICATIONS

Garvey et al., "Effects of Insulin Resistance and Type 2 Diabetes on Lipoprotein Subclass Particle Size and Concentration Determined by Nuclear Magnetic Resonance" Diabetes Feb. 2003, 52: 453-462.

(Continued)

*Primary Examiner* — Russell S Negin
(74) *Attorney, Agent, or Firm* — Kilpatrick Townsend & Stockton LLP

(57) ABSTRACT

Embodiments of the invention are directed to methods, systems and computer programs that provide improved risk stratification for people having elevated large HDL-P using at least one defined HDL risk interaction parameter.

40 Claims, 19 Drawing Sheets

(56) References Cited

OTHER PUBLICATIONS

Pascot et al., "Reduced HDL Particle Size as an Additional Feature of the Atherogenic Dyslipdemia of Abdominal Obesity" Journal of Lipid Research 2001, 42: 2007-2014.
Syvanne et al., "High Density Lipoprotein Subfractions in Non-insulin Dependent Diabetes mellitus and Coronary Artery Disease" Journal of Lipid Research 1995, 36: 573-582.
Jensen et al. "Apolipoprotein C-III as a Potential Modulator of the Association Between HDL-Cholesterol and Incident Coronary Heart Disease", *J Am Heart Assoc.* 2012;1:e000232 doi: 10.1161/JAHHA.111.000232, 10 pages.
Kaess et al. "Large-Scale Candidate Gene Analysis of HDL Particle Features", *PLoS ONE*, Jan. 2011, vol. 6, Issue 1, e14529, 9 pages.
Soininen et al. "High-throughput serum NMR metabonomics for cost-effective holistic studies on systemic metabolism", *The Royal Society of Chemistry, Analyst*, 2009, 134, 1781-1785.
Farmer et al. "Evolving Concepts of the Role of High-Density Lipoprotein in Protection from Atherosclerosis", *Curr Atheroscler Rep.*, (2011) 13:107-114.
Fogelman "When good cholesterol goes bad", *Nature Medicine*, vol. 10, No. 9, Sep. 2004, 902-903.
Jeyarajah et al. "Lipoprotein particle analysis by nuclear magnetic resonance spectroscopy", *Clin Lab Med*, Dec. 2006;26(4):847-870 (Abstract Only).
Kaess et al. "The lipoprotein subfraction profile: heritability and identification of quantitative trait loci", *Journal of Lipid Research*, vol. 49, 2008, 715-723.
Khera et al. "Cholesterol Efflux Capacity, High-Density Lipoprotein Function, and Atherosclerosis", *N Engl J Med*, 2011;364:127-135.
Navab et al. "HDL and cardiovascular disease: atherogenic and atheroprotective mechanisms", *Nat Rev Cardiol*, Apr. 2011;8(4):222-232 (Abstract Only).
Sacks et al. "Cardiovascular Endocrinology 4. Low-Density Lipoprotein Size and Cardiovascular Disease: A Reappraisal", *The Journal of Clinical Endocrinology & Metabolism*, 88(10):4525-4532, 2003.
Suna et al. "H NMR metabonomics of plasma lipoprotein subclasses: elucidation of metabolic clustering by self-organising maps", *NMR Biomed.* 2007; 20:658-672.
van der Steeg et al. "High-Density Lipoprotein Cholesterol, High-Density Lipoprotein Particle Size, and Apolipoprotein A-I: Significance for Cardiovascular Risk", *Journal of the American College of Cardiology*, vol. 51, No. 6, 2008, 634-642.
Wilson et al. "Impact of national guidelines for cholesterol risk factor screening. The Framingham Offspring Study", *JAMA*, Jul. 7, 1989; 262(1):41-44 (Abstract Only).

* cited by examiner

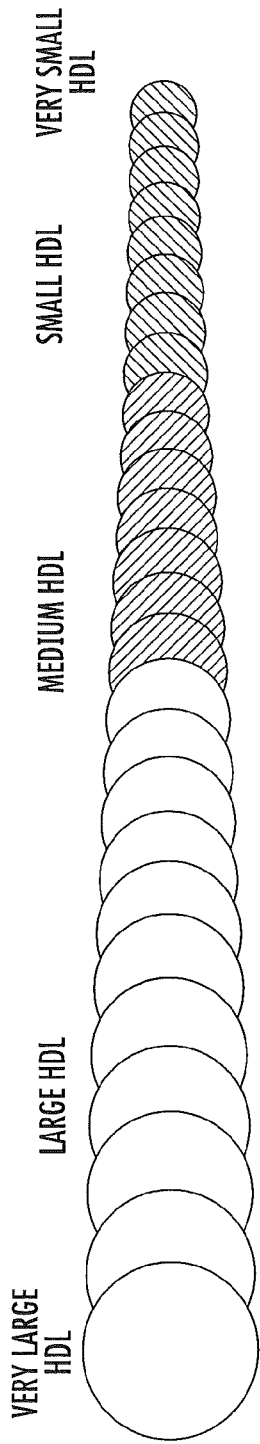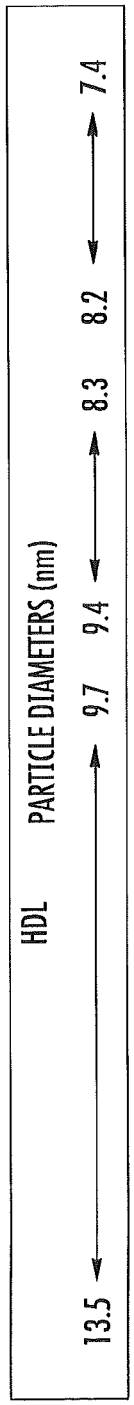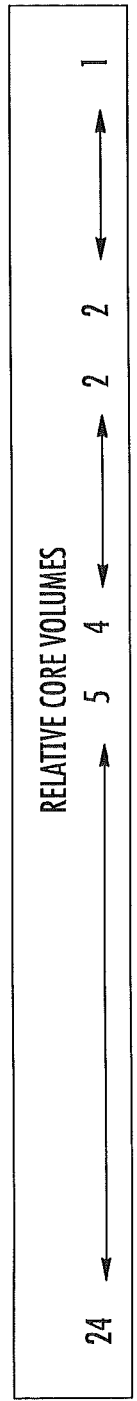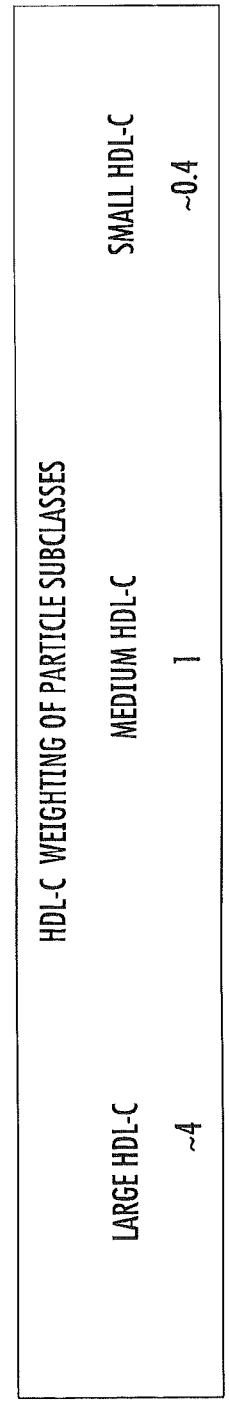
FIG. 4

NMR HDL SUBPOPULATION GROUPING AND NOMENCLATURE

| HDL DECONVOLUTION MODEL COMPONENTS | | HDL SUBPOPULATIONS | | | CHD SUBCLASS GROUPINGS* | |
|---|---|---|---|---|---|---|
| COMPONENT NAME | ESTIMATED DIAMETER (nm) | COMPONENT NAME | SUBPOPULATION NAME | ESTIMATED DIAMETER (nm) | DESCRIPTIVE NAME | ALTERNATIVE SUBCLASS NAMES |
| H1 | 7.4 | H1-2 | HP1 | 7.4-7.5 | VERY SMALL (<7.6 nm) | $H_{1-2}$, $HP_1$, $HP_{VS}$ |
| H2 | 7.5 | | | | | |
| H3 | 7.6 | H3-5 | HP2 | 7.6-7.9 | SMALL (7.6-8.2 nm) | $H_{3-8}$, $HP_{2-3}$, $HP_S$ |
| H4 | 7.8 | | | | | |
| H5 | 7.9 | | | | | |
| H6 | 8.0 | H6-8 | HP3 | 8.0-8.2 | | |
| H7 | 8.1 | | | | | |
| H8 | 8.2 | | | | | |
| H9 | 8.3 | H9-11 | HP4 | 8.3-8.5 | MEDIUM + LARGE (8.3-10.9 nm) | $H_{9-20}$, $HP_{4-7}$, $HP_{ML}$ |
| H10 | 8.4 | | | | | |
| H11 | 8.5 | | | | | |
| H12 | 8.6 | H12-14 | HP5 | 8.6-9.3 | | |
| H13 | 9.0 | | | | | |
| H14 | 9.2 | | | | | |
| H15 | 9.4 | H15-17 | HP6 | 9.4-10.2 | | |
| H16 | 9.7 | | | | | |
| H17 | 10.0 | | | | | |
| H18 | 10.5 | H18-20 | HP7 | 10.3-10.9 | | |
| H19 | 10.6 | | | | | |
| H20 | 10.8 | | | | | |
| H21 | 11.0 | H21-23 | HP8 | 11.0-12.2 | VERY LARGE (≥11.0 nm) | $H_{21-26}$, $HP_{8-9}$, $HP_{VL}$ |
| H22 | 11.5 | | | | | |
| H23 | 12.0 | | | | | |
| H24 | 12.5 | H24-26 | HP9 | 12.3-13.5 | | |
| H25 | 13.0 | | | | | |
| H26 | 13.5 | | | | | |

*SUBPOPULATION GROUPINGS AS GUIDED BY CHD RISK ASSOCIATION IN MESA.

FIG. 7

PREDICTION OF CHD EVENTS (n=42) IN MESA SUBGROUP (n=1145) WITH $HP_{VL}>80^{th}$ PERCENTILE (>1.84 μmol/L), USING LOGISTIC REGRESSION MODELS ADJUSTED FOR AGE, GENDER, RACE, SMOKING, SBP, HYPERTENSION MEDICATION, BMI, DIABETES, LDL-P AND LOG TRIGLYCERIDES.

| MODEL | HDL PARAMETER | MODEL $\chi^2$ | PARAMETER $\chi^2$ | P |
|---|---|---|---|---|
| BASE MODEL | --- | 27.9 | --- | --- |
| P1 = $HP_{VS} \times HP_{ML}$ | $HP_{VS} \times HP_{ML}$ | 32.3 | -3.84 | 0.05 |
| R1 = $HP_{VL} / HP_{ML}$ | $HP_{VL} / HP_{ML}$ | 34.7 | 5.78 | 0.02 |
| P1 + R1 | $HP_{VS} \times HP_{ML}$ | 38.0 | -2.98 | 0.08 |
|  | $HP_{VL} / HP_{ML}$ |  | 5.1 | 0.02 |
| P1/R1 | $(HP_{VS}/HP_{VL})(HP_{ML})^2$ | 37.4 | -6.99 | 0.008 |

FIG. 8A

PREDICTION OF CHD EVENTS (n=23) IN MESA SUBGROUP (n=575) WITH $HP_{VL}>90^{th}$ PERCENTILE (>2.71 μmol/L), USING LOGISTIC REGRESSION MODELS ADJUSTED FOR AGE, GENDER, RACE, SMOKING, SBP, HYPERTENSION MEDICATION, BMI, DIABETES, LDL-P AND LOG TRIGLYCERIDES.

| MODEL | HDL PARAMETER | MODEL $\chi^2$ | PARAMETER $\chi^2$ | P |
|---|---|---|---|---|
| BASE MODEL | --- | 29.7 | --- | --- |
| P1 = $HP_{VS} \times HP_{ML}$ | $HP_{VS} \times HP_{ML}$ | 30.8 | -1.04 |  |
| R1 = $HP_{VL} / HP_{ML}$ | $HP_{VL}/HP_{ML}$ | 33.5 | 3.25 | 0.07 |
| P1 + R1 | $HP_{VS} \times HP_{ML}$ | 34.3 | -0.77 |  |
|  | $HP_{VL}/HP_{ML}$ |  | 3.03 | 0.08 |
| P1/R1 | $(HP_{VS}/HP_{VL})(HP_{ML})^2$ | 31.8 | -1.64 |  |

FIG. 8B

POTENTIAL "ATHEROGENIC" OR NON-PROTECTIVE HDL-P PARAMETERS (A-HDL-Ps)

| | A1-HDL-P | A2-HDL-P |
|---|---|---|
| HDL SUBCLASS | $HDL_{26-21}$ | $HDL_{24-23}$ |
| MEDIAN (μmol/L) | 0.90 | 0.07 |
| INTERQUARTILE RANGE | 0.45-1.63 | 0-0.21 |
| CONTINUOUS ASSOCIATION WITH CHD* | | |
| MODEL $x^2$ | 235.9 | 236.7 |
| PARAMETER $x^2$ | +3.3 | +4.4 |
| HR PER 1-SD | 1.128 | 1.123 |
| P VALUE | 0.068 | 0.036 |
| DICHOTOMOUS ASSOCIATION WITH CHD* (HR) | | |
| HR (95%CI) >80$^{th}$ PERCENTILE | 1.09 (0.77-1.56) (p=0.62) | 0.94 (0.69-1.27) (p=0.68) |
| HR (95%CI) >90$^{th}$ PERCENTILE | 1.41 (0.89-2.22) (p=0.14) | 1.22 (0.84-1.78) (p=0.29) |
| HR (95%CI) >95$^{th}$ PERCENTILE | 1.60 (0.89-2.87) (p=0.12) | 1.21 (0.72-2.04) (p=0.47) |

*FROM COX REGRESSION IN MESA (289 CHD EVENTS) ADJUSTED FOR AGE, SEX, ETHNICITY, SMOKING, SBP, HYPERTENSION TREATMENT, BMI, DM, logTG, LDL-P, P1-HDL-P.

FIG. 9

CHD RISK STRATIFICATION EVALUATIONS FOR SUBJECTS WITH HIGH LEVELS OF LARGE HDL-P

RELATED APPLICATIONS

This application claims priority to and the benefit of U.S. Provisional Application Ser. No. 61/639,508, filed Apr. 27, 2012, the contents of which are hereby incorporated by reference as if recited in full herein.

FIELD OF THE INVENTION

The present invention relates generally to analysis of lipoprotein constituents in blood plasma and serum.

BACKGROUND OF THE INVENTION

NMR spectroscopy has been used to concurrently measure very low density lipoprotein (VLDL), low density lipoproteins (LDL) and high density lipoproteins (HDL) as VLDL, LDL and HDL particle subclasses from in vitro blood plasma or serum samples. See, FIG. 1 and U.S. Pat. Nos. 4,933,844 and 6,617,167, the contents of which are hereby incorporated by reference as if recited in full herein. Generally stated, to evaluate the lipoproteins in a blood plasma and/or serum sample, the amplitudes of a plurality of NMR spectroscopy derived signals within a chemical shift region of the NMR spectrum are derived by deconvolution of the composite methyl signal envelope or spectrum to yield subclass concentrations.

The subclasses are represented by many (typically over 60) discrete contributing subclass signals associated with NMR frequency and lipoprotein diameter as shown in FIG. 2. As shown in FIG. 3, the NMR evaluations can interrogate the NMR signals to produce concentrations of different subpopulations shown as seventy-three (73) discrete subpopulations, 27 for VLDL, 20 for LDL and 26 for HDL. These sub-populations can be further characterized as associated with a particular size range within the VLDL, LDL or HDL subclasses.

Conventionally, a patient's overall risk of coronary heart disease (CHD) and/or coronary artery disease (CAD) has been assessed based on measurements of cholesterol content of a patient's LDL and HDL particles (LDL-C, HDL-C) rather than the numbers of these particles. These two risk factors are used to assess a patient's risk, and treatment decisions may be made to reduce the "bad" cholesterol (LDL-C) or increase the "good" cholesterol (HDL-C).

In the past, the LipoProfile® "advanced" lipoprotein test panels from LipoScience, Inc. have typically included a total high density lipoprotein particle (HDL-P) measurement (e.g., HDL-P number) and a total low density lipoprotein particle (LDL-P) measurement (e.g., LDL-P number). The particle numbers represent the concentration in units such as nmol/L (for LDL-P) or µmol/L (for HDL-P). A total HDL-P number, the sum of the concentration values of each of the HDL-P subclasses, can provide CHD risk assessment information that may be more accurate than or complement HDL-C.

It is believed that LDL-P is a better indicator of risk of CHD relative to LDL-C as well as for therapy decisions. However, there are still open questions about the different functions of HDL and how to best evaluate CHD risk associated with a patient's HDL. See, e.g., Kher at el., Cholesterol Efflux Capacity, High-Density Lipoprotein Function, and Atherosclerosis, N Engl. J. Med. 364: 127-135 (Jan. 13, 2011); Navab et al., HDL and cardiovascular disease: atherogenic and atheroprotective mechanisms, Nat. Rev. Cardiol., 8, 222-232 (2011); and Alan Fogelman, When good cholesterol goes bad, Nat. Med., Vol. 10, No. 9, pp. 902-903 (September 2004), the contents of which are hereby incorporated by reference as if recited in full herein. The mechanisms by which HDL can be protective or non-protective as associated with a person's risk of developing atherosclerosis or heart disease are complex and multifactorial. See, Farmer et al., Evolving Concepts of the Role of High-Density Lipoprotein in Protection from Athersclerosis, Curr Atheroscler Rep (2011) 13:107-114, the contents of which are hereby incorporated by reference as if recited in full herein.

Van der Steeg et al. have carried out studies showing that higher HDL-C levels when observed with a preponderance of large HDL particles are not inversely related to the risk of CAD. Indeed, higher HDL-C proved to be a major cardiac event risk factor when adjusted for age, gender, smoking, apoA-1 and apoB. Van der Steeg et. al. concludes that when apoA-1 and apoB are kept constant, HDL-C and HDL particle size may confer risk at very high values. See, Van der Steeg et. al., High-Density Lipoprotein Cholesterol, High Density Lipoprotein Particle Size, and Apolipoprotein A-1: Significance for Cardiovascular Risk, JACC, Vol. 51, No. 6, 2008 (634-642), the contents of which are hereby incorporated by reference as if recited in full herein.

There remains an unmet clinical need for tests that can identify those individuals that have high levels of HDL, e.g., large HDL-P and that may be at increased risk of a cardiac event.

SUMMARY

Embodiments of the invention are directed at methods, systems, and computer program products for screening, assessing and/or evaluating whether a person having (i) a high level of HDL-C and along with elevated concentrations of very large HDL-P or (ii) elevated concentrations of very large HDL-P is at risk of having or developing at least one of CHD, stroke or atherosclerosis.

Embodiments of the invention provide an NMR screening test to identify whether a person having a high level of very large HDL-P may be at increased risk of having or developing at least one of CVD, CHD, stroke or atherosclerosis.

Embodiments of the invention carry out a screening, assessment and/or evaluation only on patients having elevated levels of very large HDL particle subclasses (H21-H26) at ≥80% of a population norm.

Embodiments of the invention can be applied to patient evaluations only when HDL-C is above 60 mg/dL, then when they also have elevated levels at ≥80% of a population norm of very large HDL particle subclasses (H21-H26).

The screening, assessment and/or evaluation test can employ at least one defined interaction HDL risk parameter that includes a sum, product or ratio of two or more of the following: $HP_{VL}$, $HP_{VS}$ and $HP_{ML}$.

The screening, assessment and/or evaluation test can include at least one of P1 ($HP_{VS} \times HP_{ML}$) or R1 ($HP_{VL}/HP_{ML}$) as an HDL risk parameter.

The screening, assessment and/or evaluation test can include both P1 and R1.

The screening, assessment and/or evaluation test can include P1/R1 and patients having a value in the first quartile or the first and second quartile are identified as at increased risk.

Certain embodiments of the present invention are directed at providing methods, systems, and computer program products that discriminate between subclasses of HDL particles of a discrete size range taken from a blood plasma or serum sample to facilitate patient risk stratification for patients presenting with high levels of very large HDL-P subclasses.

Some embodiments are directed to methods of determining whether a subject with elevated concentrations of very large high density lipoprotein (HDL) particles (HDL-P) is at increased risk for a cardiac event and/or CHD. The methods include programmatically calculating at least one HDL interaction risk parameter associated with HDL content of a blood plasma or serum sample of the subject. The at least one HDL interaction risk parameter includes at least two of $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses.

The at least one HDL interaction risk parameter can include P1 or R1, or P1 and R1, wherein P1 is a product defined by $HP_{VS} \times HP_{ML}$, and wherein R1 is a ratio defined by $HP_{VL}/HP_{ML}$.

The at least one HDL interaction risk parameter can include at least one of the following: $(HP_{VS})(HP_{ML})/(HP_{VL})$, or $((HP_{VS})(HP_{ML})^2)/(HP_{VL})$, or $(HP_{ML})^2/(HP_{VL})$, wherein P1 is a product defined by $HP_{VS} \times HP_{ML}$, and wherein R1 is a ratio defined by $HP_{VL}/HP_{ML}$.

The method may include electronically identifying when a subject has an elevated concentration of $HP_{VL}$ relative to a population norm, wherein the subject has an elevated concentration of $HP_{VL}$ when a respective concentration is ≥80% of a population norm, and wherein the programmatic calculation is electronically selectively carried out only when the subject has the elevated concentration of $HP_{VL}$.

The method may include screening subjects that may benefit from an HDL risk stratification test by (a) first identifying if the subject has elevated high density lipoprotein-cholesterol (HDL-C) that is at least one of: ≥60 mg/dL, ≥80 mg/dL, or ≥100 mg/dL; then (b) electronically identifying when the subject also has an elevated concentration of $HP_{VL}$ that is ≥80% of a population norm, and wherein the performing the programmatic calculation is selectively carried out only if the subject has the elevated concentration of $HP_{VL}$.

The $HP_{VS}$ can include HDL subpopulations having a size between 7.4 nm and 7.6 nm (average).

The $HP_{ML}$ can include HDL subpopulations having a size between 8.3 nm-10.9 nm (average).

The $HP_{VL}$ can include HDL subpopulations having a size between 11 nm to 13.5 nm (average).

The method can include deconvolving an NMR composite signal into 26 subpopulations (H1-H26) of different sizes of HDL-P ranging from a smallest HDL-P size associated with H1 to a largest HDL-P size associated with H26, then:

electronically calculating concentrations of H1 and H2 to generate the $HP_{VS}$;

electronically calculating concentrations of H9-H20 to generate the $HP_{ML}$; and electronically calculating concentrations of H21 and H26 to generate the $HP_{VL}$.

The programmatically calculated at least one HDL interaction risk parameter can include P1/R1.

A respective subject can be identified as at risk for CHD if P1/R1 has a value in the first or second quartile of a population norm.

A respective subject can be identified as at risk for CHD if P1/R1 has a value ≤170 $\mu mol^2/L^2$.

The method can include generating a report that visually and/or textually indicates whether a respective subject is at increased risk of CHD despite having elevated $HP_{VL}$.

The method can include generating a report based on the programmatic calculation of the at least one HDL interaction risk parameter includes at least one of the following: R1, P1, P1/R1, or P1+R1.

The method can include electronically monitoring whether there is a change in the HDL risk interaction parameter over time to assess a change in CHD risk when $HP_{VL}$, remains above 1.84 µmol/L.

The method can include referring the subject for further medical evaluation if the programmatic calculation indicates there is a likelihood of increased risk of CHD despite the elevated large HDL-P.

The subject can be human.

The method can include obtaining NMR signal data of an in vitro blood plasma or serum sample of the subject to determine NMR derived concentration measurements. The obtaining and calculating steps can be carried out using at least one processor. The method can include providing a report indicating whether a respective subject is at risk of having and/or developing CHD based, in part, on the programmatic calculation.

Other embodiments are directed to computer program products for stratifying CHD risk for patients with elevated concentrations of very large high density lipoprotein (HDL) particles (HDL-P). The computer program products can include a non-transitory computer readable storage medium having computer readable program code embodied in the medium. The computer-readable program code includes: (a) computer readable program code that obtains concentration measurements of at least twenty subpopulations of HDL-P subclasses in a blood plasma or serum sample; and (b) computer readable program code that calculates at least one HDL interaction risk parameter associated with HDL content of a blood plasma or serum sample of the subject. The at least one HDL interaction risk parameter includes at least two of $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses.

The at least one HDL interaction risk parameter can include P1 or R1, or P1 and R1. P1 is a product defined by $HP_{VS} \times HP_{ML}$, and R1 is a ratio defined by $HP_{VL}/HP_{ML}$.

The at least one HDL interaction risk parameter can include at least one of the following: $(HP_{VS})(HP_{ML})/(HP_{VL})$, or $((HP_{VS})(HP_{ML})^2)/(HP_{VL})$, or $(HP_{VL})^2/(HP_{VL})$, wherein P1 is a product defined by $HP_{VS} \times HP_{ML}$, and wherein R1 is a ratio defined by $HP_{VL}/HP_{ML}$.

The computer readable program code can include computer readable program code that identifies when a subject has an elevated concentration of $HP_{VL}$ relative to a population norm. The subject can have an elevated concentration of $HP_{VL}$ when a respective concentration is ≥80% of a population norm. The computer readable program code that calculates the at least one HDL interaction risk factor can be configured to selectively be performed only when the subject has the elevated concentration of $HP_{VL}$.

The computer program product can include comprising computer readable program code that screens subjects that may benefit from an HDL risk stratification test by (a) first identifying if the subject has elevated high density lipoprotein-cholesterol (HDL-C) that is at least one of: ≥60 mg/dL, ≥80 mg/dL, or ≥100 mg/dL; then (b) electronically identifying when the subject also has an elevated concentration of $HP_{VL}$ that is ≥80% of a population norm, then directing the programmatic calculation if the subject has the elevated concentration of $HP_{VL}$.

The $HP_{VS}$ includes HDL subpopulations having a size between 7.4 nm and 7.6 nm (average), wherein the $HP_{ML}$ includes HDL subpopulations having a size between 8.3 nm-10.9 nm (average), and wherein the $HP_{VL}$ includes HDL subpopulations having a size between 11 nm to 13.5 nm (average).

The computer program product can include computer readable program code configured to deconvolve an NMR composite signal into 26 subpopulations (H1-H26) of different sizes of HDL-P ranging from a smallest HDL-P size associated with H1 to a largest HDL-P size associated with H26, then:

calculate concentrations of H1 and H2 to generate the $HP_{VS}$;

calculate concentrations of H9-H20 to generate the $HP_{ML}$; and calculate concentrations of H21 and H26 to generate the $HP_{VL}$.

The at least one HDL interaction risk parameter includes P1/R1.

A respective subject can be identified as at risk for CHD if P1/R1 has a value in the first or second quartile of a population norm.

A respective subject can be identified as at risk for CHD if P1/R1 has a value ≤170 $\mu mol^2/L^2$.

The computer program product can include program code that generates a report that visually and/or textually indicates whether a respective subject is at increased risk of CHD despite having elevated $HP_{VL}$.

The computer program product can include computer program code that generates a report including at least one of the following as the at least one HDL interaction risk parameter: R1, P1, P1/R1, or P1+R1.

The computer program product can include computer readable program code configured to electronically generate a graph showing, provide data representing and/or monitor whether there is a change in the HDL risk interaction parameter of a respective subject over time to assess a change in CHD risk when $HP_{VL}$ remains above 1.84 µmol/L.

The product can include computer readable program code that obtains NMR signal data of an in vitro blood plasma or serum sample of the subject to determine NMR derived concentration measurements and computer readable program code that provides a report indicating whether a respective subject is at risk of having and/or developing CHD based, in part, on the at least one HDL interaction risk parameter.

Still other embodiments are directed to systems for analyzing CHD risk. The systems include a circuit comprising at least one processor configured to determine whether a subject with elevated concentrations of very large high density lipoprotein (HDL) particles (HDL-P) is at increased risk for a cardiac event and/or CHD. The at least one processor is configured to calculate at least one HDL interaction risk parameter associated with HDL content of a blood plasma or serum sample of the subject, the at least one HDL interaction risk parameter that includes at least two of $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses.

The circuit can be onboard or in communication with an NMR spectrometer for acquiring at least one NMR spectrum of an in vitro blood plasma or serum sample.

The at least one HDL interaction risk parameter can include P1 or R1, or P1 and R1 (or both). P1 is a product defined by $HP_{VS} \times HP_{ML}$ and R1 is a ratio defined by $HP_{VL}/HP_{ML}$.

The at least one HDL interaction risk parameter can include at least one of the following: $(HP_{VS})(HP_{ML})/(HP_{VL})$, or $((HP_{VS})(HP_{ML})^2)(HP_{VL})$, or $(HP_{ML})^2/(HP_{VL})$; wherein P1 is a product defined by $HP_{VS} \times HP_{ML}$, and wherein R1 is a ratio defined by $HP_{VL}/HP_{ML}$.

The at least one processor can be configured to identify when a subject has an elevated concentration of $HP_{VL}$ relative to a population norm, wherein the subject has an elevated concentration of $HP_{VL}$ when a respective concentration is ≥80% of a population norm, and wherein the at least one processor is configured to provide a CHD risk assessment using the at least one HDL interaction risk parameter only when the subject has the elevated concentration of $HP_{VL}$.

The at least one processor is configured to screen subjects that may benefit from an HDL risk stratification test by (a) first identifying if the subject has elevated high density lipoprotein-cholesterol (HDL-C) that is at least one of: ≥60 mg/dL, ≥80 mg/dL, or ≥100 mg/dL; then (b) identifying when the subject also has an elevated concentration of $HP_{VL}$ that is ≥80% of a population norm.

The $HP_{VS}$ can include HDL subpopulations having a size between 7.4 nm and 7.6 nm (average), wherein the $HP_{ML}$ includes HDL subpopulations having a size between 8.3 nm-10.9 nm (average), and the $HP_{VL}$ can include HDL subpopulations having a size between 11 nm to 13.5 nm (average).

The at least one processor can be configured to deconvolve an NMR composite signal into 26 subpopulations (H1-H26) of different sizes of HDL-P ranging from a smallest HDL-P size associated with H1 to a largest HDL-P size associated with H26, then:

calculate concentrations of H1 and H2 to generate the $HP_{VS}$;

calculate concentrations of H9-H20 to generate the $HP_{ML}$; and calculate concentrations of H21 and H26 to generate the $HP_{VL}$.

The at least one HDL interaction risk parameter can include P1/R1.

A respective subject can be identified as at risk for CHD if P1/R1 has a value in the first or second quartile of a population norm.

A respective subject can be identified as at risk for CHD if P1/R1 has a value ≤170 $\mu mol^2/L^2$.

The at least one processor can be configured to generate a report that visually and/or textually indicates whether a respective subject is at increased risk of CHD despite having elevated $HP_{VL}$.

The at least one HDL interaction risk parameter can include at least one of the following: R1, P1, P1/R1, or P1+R1.

The at least one processor can be configured to monitor whether there is a change in the at least one HDL risk interaction parameter over time to assess a change in CHD risk when $HP_{VL}$ remains above 1.84 µmol/L.

The at least one processor can be configured to obtain NMR signal data of an in vitro blood plasma or serum sample of the subject to determine NMR derived concentration measurements, then provide a report indicating whether a respective subject is at risk of having and/or developing CHD based, in part, on the calculated at least one HDL interaction risk parameter.

Still other embodiments are directed to patient test reports. The reports include at least one HDL risk interaction parameter that indicates whether a patient having elevated concentrations of very large high density lipoprotein (HDL) particles (HDL-P) is at increased risk for a cardiac event and/or CHD. The at least one HDL interaction risk parameter includes at least two of $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses.

The at least one HDL interaction risk parameter can include P1 or R1, or P1 and R1, wherein P1 is a product defined by $HP_{VS} \times HP_{ML}$, R1 is a ratio defined by $HP_{VL}/HP_{ML}$.

The at least one HDL interaction risk parameter can include at least one of the following: $(HP_{VS})(HP_{ML})/(HP_{VL})$, or $((HP_{VS})(HP_{ML})^2)(HP_{VL})$, or $(HP_{ML})^2/(HP_{VL})$, wherein P1 is a product defined by $HP_{VS} \times HP_{ML}$, and wherein R1 is a ratio defined by $HP_{VL}/HP_{ML}$.

The test report can include an elevated concentration of $HP_{VL}$, relative to a population norm. The subject can have an elevated concentration of $HP_{VL}$ when a respective concentration is ≥80% of a population norm.

The report can visually indicate when the subject has (i) elevated high density lipoprotein-cholesterol (HDL-C) that is at least one of: ≥60 mg/dL, ≥80 mg/dL, or ≥100 mg/dL and (ii) an elevated concentration of $HP_{VL}$ that is ≥80% of a population norm.

The at least one HDL interaction risk parameter can include P1/R1.

The report can visually indicate that a respective subject is identified as at risk for CHD if P1/R1 has a value in the first or second quartile of a population norm.

The report can visually indicate that a respective subject is identified as at risk for CHD if P1/R1 has a value ≤170 $\mu mol^2/L^2$.

The report can include the at least one HDL interaction risk parameter that includes at least one of the following: R1, P1, P1/R1, or P1+R1.

The report can include graph that shows whether there is a change in the at least one HDL risk interaction parameter over time to assess a change in CHD risk when $HP_{VL}$ remains above 1.84 µmol/L.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 4 is a schematic illustration of HDL particle size with respect to associated diameters, relative core volumes and HDL weighting of particle subclasses.

FIG. 7 is a table of H1-H26 illustrating the HDL subpopulation groupings and nomenclature including the 9 subpopulations HP1-HP9 shown in FIGS. 6B and 6C and the four subclass HDL groupings shown in FIG. 6D selected for association with CHD according to embodiments of the present invention.

FIG. 8A compares the prediction of CHD events (n=42/1145), as given by the model χ2 values, of logistic models without (base model) and with different HDL parameters, with analysis restricted to individuals in MESA having elevated concentrations (above the 80$^{th}$ percentile; >1.84 μmol/L) of very large HDL particles, H21-H26, according to embodiments of the present invention.

FIG. 8B is a table containing the same information as FIG. 8A, but with analysis restricted to a smaller group of individuals (n=23/575) having even more elevated concentrations (above the 90$^{th}$ percentile; >2.71 μmol/L) of very large HDL particles, H21-H26, according to embodiments of the present invention. It is noted that this chart is provided by way of example only as the number of events n=23 make the statistical confidence in the results less reliable; additional or larger study populations may improve these values.

FIG. 9 is a chart of very large HDL-P parameters H21-26 and H23-24 illustrating median and interquartile ranges and HR (Hazard Ratio) for 289 coronary events from a Cox regression analysis adjusted for the noted parameters according to embodiments of the present invention.

Figure 1:
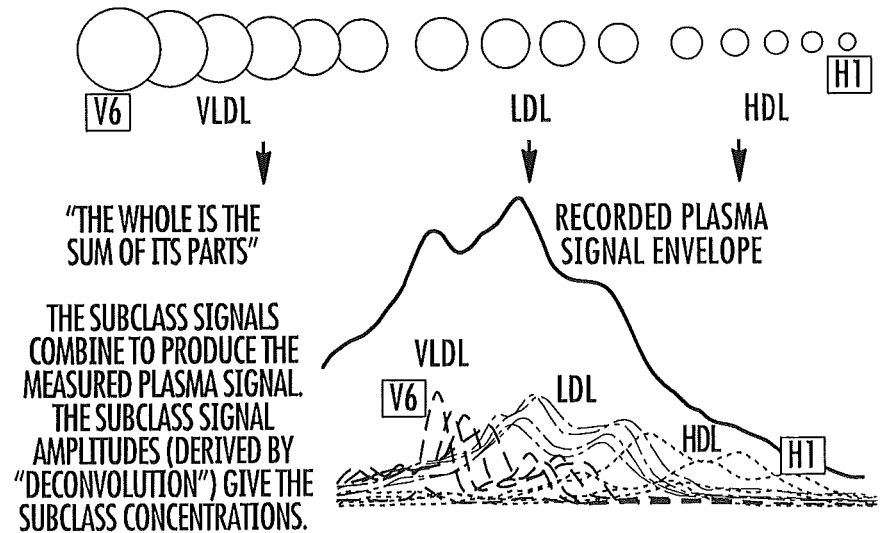
FIG. 1 is a schematic illustration of lipoprotein subclasses and the chemical shift spectra of a representative sample of lipoprotein constituent subclasses with a composite plasma signal envelope and subclass signals that can be used for subclass concentrations.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program directed operations. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input.

The term "about" refers to +/−10% (mean or average) of a specified value or number.

The term "circuit" refers to an entirely software embodiment or an embodiment that includes a combination of software and hardware components. The circuit can be a distributed system using a wireless and/or internet connection or a system that resides on one apparatus.

The terms CAD and CHD are used interchangeably and broadly to refer to a patient or subject's risk of developing or having coronary artery and/or coronary heart disease or other negative cardiac event.

The terms "population norm" and "standard" value associated with a lipoprotein measurement can be the values defined by a large study such as the Framingham Offspring Study or the Multi-Ethnic Study of Atherosclerosis (MESA). However, the instant invention is not limited to these population values as the presently defined normal or high ranges of at-risk population values (e.g. concentrations or levels) may change over time.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

As is generally accepted, HDL-cholesterol and/or LDL-cholesterol levels provided by conventional lipid panels fail to sufficiently differentiate populations with and without elevated risk for CHD or CAD. As is known to those of skill in the art, the Framingham study proposed a relatively lengthy risk model that considers many factors such as age, gender, smoking habits, as well as cholesterol values. The research conducted in the Framingham Offspring Study also defined normative and at-risk population values from subjects in the study. See Wilson et al., *Impact of National Guidelines for Cholesterol Risk Factor Screening. The Framingham Offspring Study*, JAMA, 1989; 262: 41-44.

The term "protective HDL-P" refers to HDL-P parameters that have a statistical probability of being inversely associated with risk of CHD and/or providing anti-atherogenic protection against one or more of atherosclerosis, CHD and/or myocardial infarction ("MI"). The term "NP-HDL" refers to HDL-P parameters which do not provide a statistical probability of inverse risk association for one or more of atherosclerosis, CHD or myocardial infarction (MI). The NP-HDL may be merely "neutral" as to being associated with an increased risk or may be considered to present a positive risk, be atherogenic and/or provide an increased risk of atherosclerosis, CHD or MI.

Lipoproteins include a wide variety of particles found in plasma, serum, whole blood, and lymph, comprising various types and quantities of triglycerides, cholesterol, phospholipids, sphyngolipids, and proteins. These various particles permit the solubilization of otherwise hydrophobic lipid molecules in blood and serve a variety of functions related to lipolysis, lipogenesis, and lipid transport between the gut, liver, muscle tissue and adipose tissue.

In blood and/or plasma, HDL has been classified in many ways, generally based on physical properties such as density or electrophoretic mobility or measures of apolipoprotein A-1 (Apo A-1), the main protein in HDL. Classification based on nuclear magnetic resonance (NMR) determined particle size can distinguish a number of discrete components for each of VLDL, HDL and LDL subclasses.

The NMR derived estimated HDL-P particle sizes for H1-H26 (FIG. 7) noted herein typically refer to average measurements, but other size demarcations may be used.

It is also noted that while NMR measurements of the lipoprotein particles are contemplated as being particularly suitable for the analyses described herein, it is contemplated that other technologies may be used to measure these parameters now or in the future and embodiments of the invention are not limited to this measurement methodology. It is also contemplated that different protocols using NMR may be used (e.g., including different deconvolving protocols) in lieu of the deconvolving protocol described herein. See, e.g., Kaess et al., The lipoprotein subfraction profile: heritability and identification of quantitative trait loci, J Lipid Res. Vol. 49 pp. 715-723 (2008); and Suna et al., 1H NMR metabolomics of plasma lipoprotein subclasses: elucidation of metabolic clustering by self-organising maps, NMR Biomed. 2007; 20: 658-672. Flotation and ultracentrifugation employing a density-based separation technique for evaluating lipoprotein particles and ion mobility analysis are alternative technologies for measuring lipoprotein subclass particle concentrations.

Generally stated, it is believed that accurate CHD risk stratification may depend on recognizing that there is a fundamentally different relationship of HDL with CHD risk depending on whether levels of the very large HDL subclass ($HP_{VL}$) are elevated or not. A subset of patients with elevated levels of $HP_{VL}$ have high CHD risk, possibly because their HDL particles are dysfunctional and/or proatherogenic. Identification of this high-risk subset can be made by calculating the relative amounts of $HP_{VL}$ and other defined HDL particle subpopulations.

Figure 2:
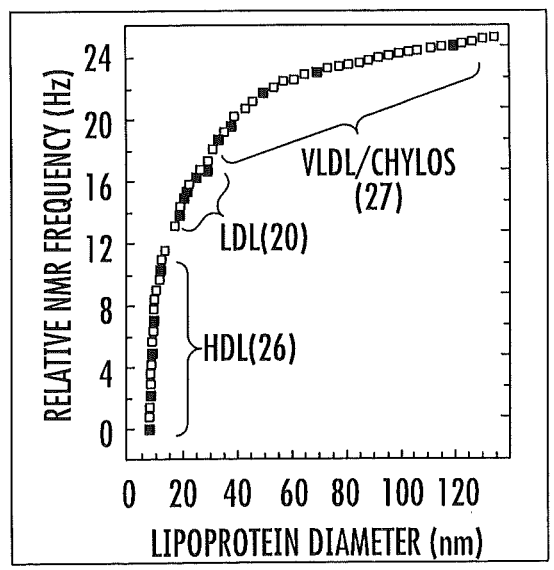
FIG. 2 is a graph of relative NMR frequency (Hz) versus lipoprotein diameter (nm) of HDL, LDL and VLDL/Chylos for 73 different subclass signals (for the 73 subpopulations).

As shown in FIGS. 1 and 2, over 20 discrete subpopulations (sizes) of lipoprotein particles, typically between about 30-80 different size subpopulations (or even more) can be measured for a blood plasma or serum sample. These discrete sub-populations can be grouped into defined subclasses. The defined subclasses can include a plurality of different subclasses, including three or more for each of VLDL and HDL and two or three or more for LDL (if the latter, with one of the three identified as IDL in the size range between large LDL and small VLDL).

Figure 3:
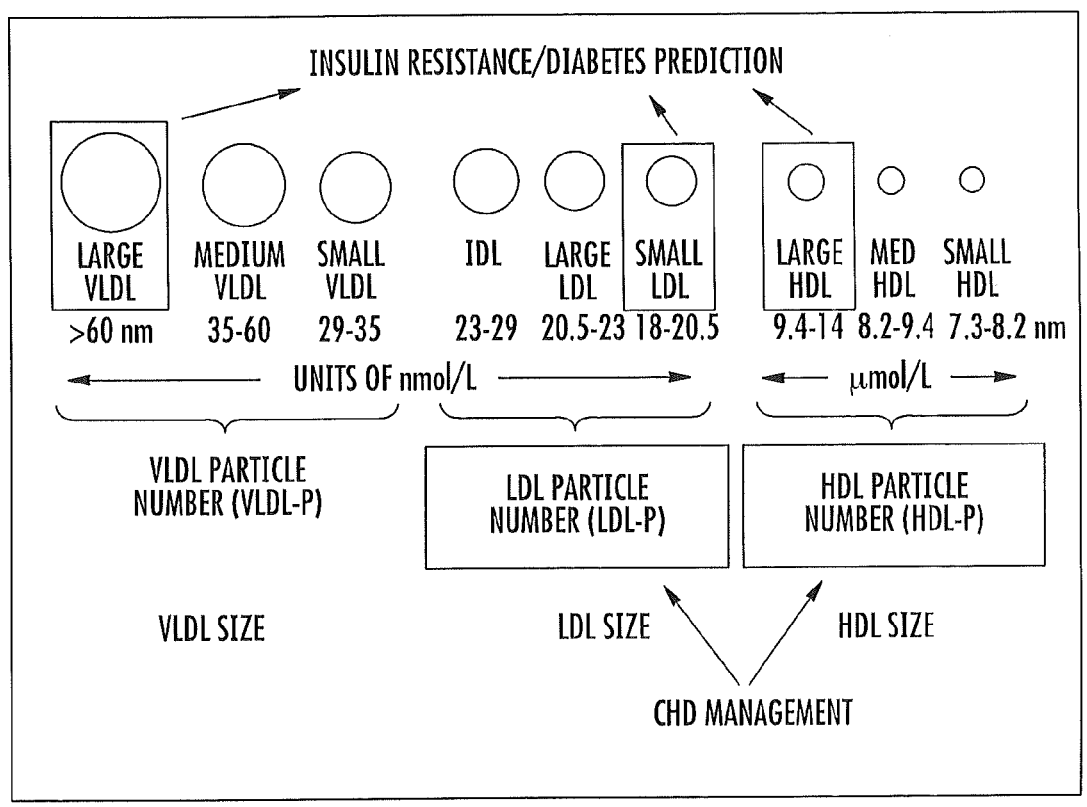
FIG. 3 is a schematic illustration of how the 73 subpopulations may be grouped into 9 subclasses to maximize their associations with insulin resistance such as for LP-IR assessments.

FIG. 3 illustrates that conventional CHD risk assessment involves LDL-P and HDL-P numbers and that insulin resistance/diabetes prediction or risk is associated with concentrations of large VLDL, small LDL and large HDL.

FIG. 4 is a schematic illustration showing that because larger HDL particles contain so much more cholesterol than smaller HDL particles, HDL-C as a risk biomarker gives much more weight to variations in the concentration of the large subpopulations and relatively undervalues differences in concentration of the smaller size subpopulations.

Embodiments of the invention classify lipoprotein particles into subclasses grouped by size ranges based on functional/metabolic relatedness as assessed by their correlations to CHD risk as shown in FIG. 6A-6D, for example.

HDL-P sizes typically range (on average) from between about 7 nm to about 15 nm, more typically about 7.3 nm to about 14 nm. The HDL subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med. 2006; 26: pp. 847-870, the contents of which are hereby incorporated by reference as if recited in full herein. The HDL-P concentration is the sum of the particle concentrations of all of the respective HDL subpopulations.

The term "very small" HDL particle subclasses ($HP_{VS}$) refers to HDL particle subclasses or HDL subpopulations with estimated (average) diameter sizes <7.6 nm, typically 7.4 nm≤$HP_{VS}$<7.6 nm.

The term "very large" HDL particle subclasses ($HP_{VL}$) refers to HDL particle subclasses or HDL subpopulations with estimated (average) diameter sizes ≥11.0 nm, typically between 13.5 nm≤$HP_{VL}$≤11.0 nm.

The term "medium plus large" HDL particle subclasses ($HP_{ML}$) refers to HDL particle subclasses or HDL subpopulations with estimated (average) diameter sizes between 8.3 nm and 10.9 nm or 10.8 nm; typically 8.3 nm≤$HP_{ML}$≤10.9 nm.

The term "small" HDL particle subclasses (HPs) refers to HDL particle subclasses or HDL subpopulations with estimated (average) diameter sizes between 7.6 to 8.2 nm.

It is contemplated that the defined estimated ranges for one or more of $HP_{VS}$, $HP_S$, $HP_{VL}$, or $HP_{ML}$ may vary by +/−0.1 nm or somewhat more, particularly when measured with alternative NMR deconvolving or other methods, without unduly affecting a statistical risk association and/or a subclass grouping.

The term "HDL interaction risk parameter" refers to a parameter that includes two or more defined subclasses of HDL that are combined into a single component/parameter and define a positive or negative statistical risk association based on a logistic regression model.

The term "CHD risk model" refers to a statistical risk model having defined parameters associated with a likelihood of having or developing CHD risk as measured by standard $\chi 2$ and/or p values (the latter with a sufficiently representative study population). The CHD risk model can be a logistic regression model.

The term "P1" refers to the product of $HP_{VS} \times HP_{ML}$ as an HDL interaction risk parameter.

The term "R1" refers to a ratio of $HP_{VL}/HP_{ML}$ as an HDL interaction risk parameter.

LDL is known to carry the so-called "bad" cholesterol. LDL particles come in different sizes. Conventionally, the smaller sizes have been thought to be the most dangerous type in that they were generally thought to be inherently more atherogenic than large particles. See, Sacks et al., *Clinical review 163: Cardiovascular endocrinology: Low density lipoprotein size and cardiovascular disease: a reappraisal*, J. Clin. Endocrinol Metab., 2003; 88: 4525-4532. Presently, LDL particle sizes are characterized as "Pattern A" (large) and "Pattern B" (small). Pattern A can be defined as large average particle sizes which typically includes sizes of between about 20.5-23.0 nm. Pattern B can be defined as smaller average particle sizes between about 18.0-20.5 nm. The LDL-P number can be defined as the sum of the small, large and IDL subclass concentrations (FIG. 3). As shown in FIGS. 3 and 4, the small LDL particles can include particles whose sizes range from between about 18.0 to about 20.5 nm. The large LDL particles can include particles ranging in diameter between about 20.5-23.0 nm. It is noted that the LDL subclasses of particles can be divided in other size ranges. In addition, intermediate-density lipoprotein particles ("IDL" or "IDL-P"), which range in diameter from approximately 23.0-29.0 nm, can be included among the particles defined as LDL.

Figure 6A:
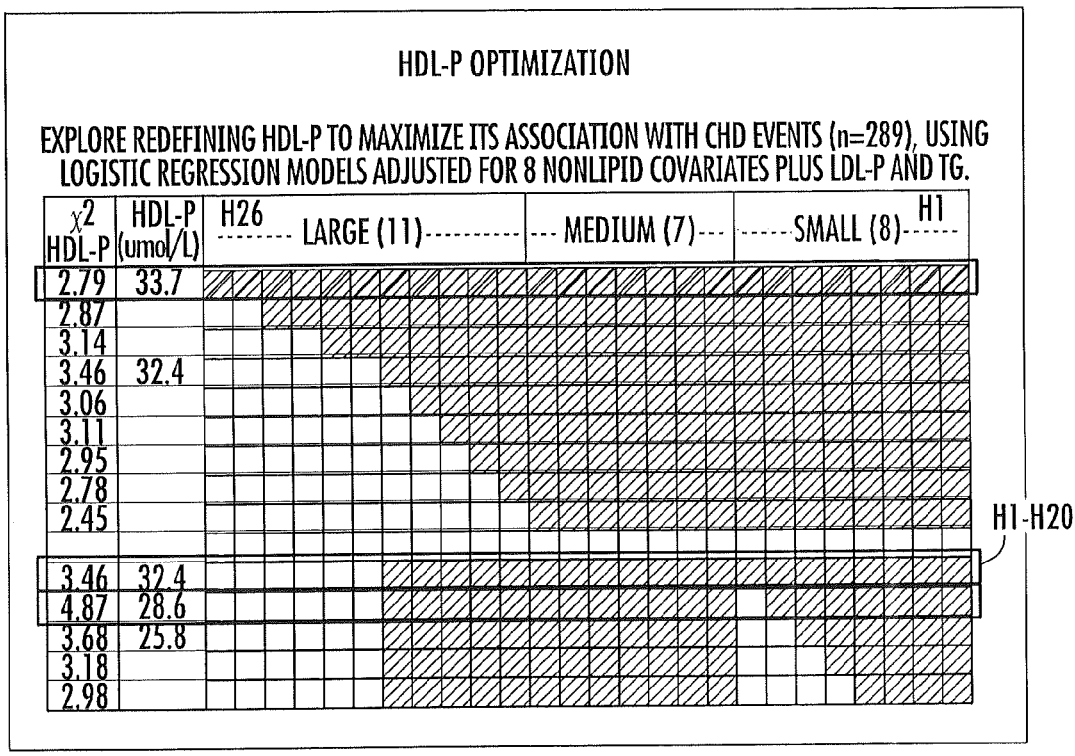
FIG. 6A is a chart showing the varying associations with CHD event risk of different groupings of the 26 HDL subpopulations to make alternate candidate versions of protective HDL-P according to embodiments of the present invention.

As shown in the chart of FIG. 6A, when the particle concentrations of all 26 of the HDL subpopulations are added together, as indicated by the shaded squares in the top row of the chart, it produces total HDL-P, the mean concentration of which is 33.7 μmol/L in the MESA study population. By omitting from total HDL-P the concentrations of the various subpopulations indicated by the non-shaded squares in the chart, 12 other groupings of HDL-P are generated. The incremental amount of CHD risk prediction given by each of these alternate versions of HDL-P was assessed in logistic regression models adjusted for 8 non-lipid covariates and LDL-P and triglycerides (TG). The $\chi 2$ values in the left-most column of the chart give a quantitative assessment of how much incremental prediction was given by inclusion of each of the alternate HDL-P parameters in the regression model. Unexpectedly, it was found that omitting the 6 largest HDL subpopulations (H21-H26) made the HDL-P parameter more predictive of CHD risk, as indicated by the increase of the $\chi 2$ value to 3.46. As shown in the bottom section of the chart, an even more robust association of the HDL-P parameter was obtained by additionally omitting the H8 subpopulation. Stated differently, in some embodiments, the "protective HDL-P" number can exclude HDL subclass components at or above about 11 nm, e.g., with sizes between about 13.5 nm to about 11 nm and/or the non-protective HDL-P are the very large HDL-P subpopulations H21-26.

FIG. 9 is a chart that identifies potential NP HDL-P parameters ("A-HDL-Ps"). When comparing two groupings of large HDL subclass components, H26-H21 versus H24-H23, both show positive risk associations with CHD. A risk assessment can be generated that considers both NP HDL-P and protective HDL-P.

Figure 6B:
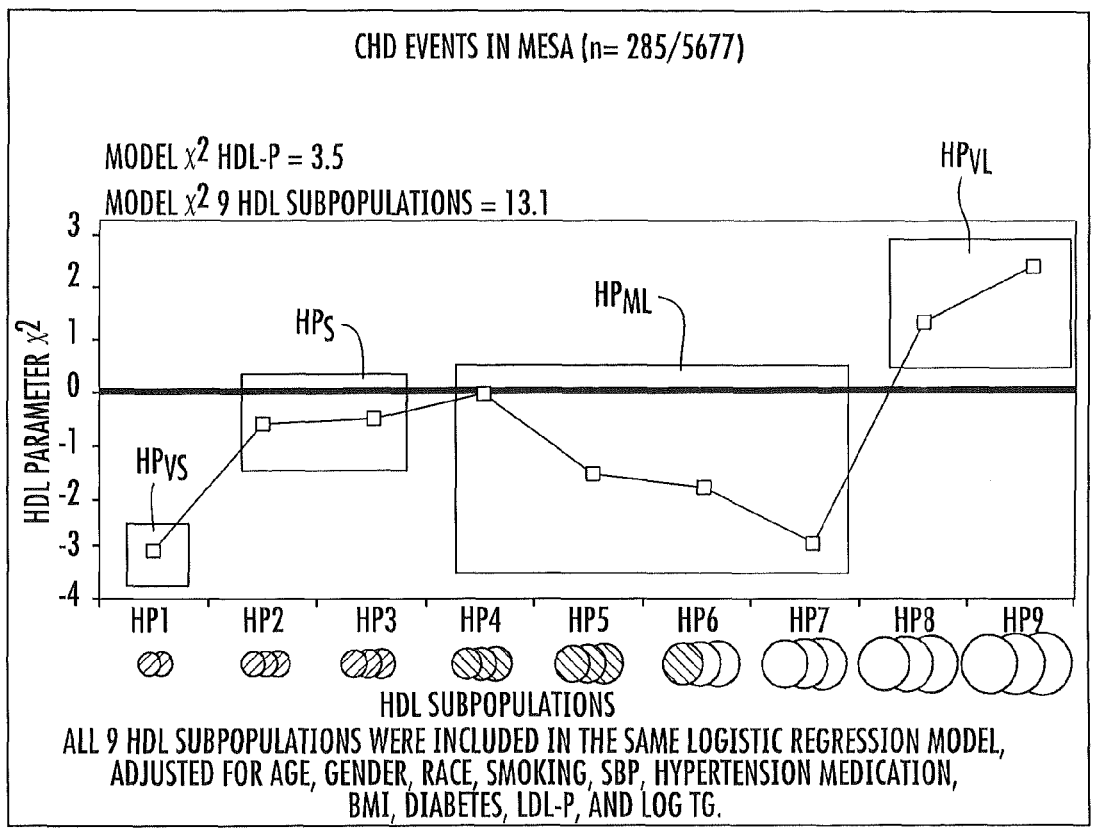
FIG. 6B is a graph illustrating CHD risk associations for each of 9 different size groupings of the 26 HDL subpopulations and four boxes of further groupings according to embodiments of the present invention, with the χ2 values from the logistic regression model indicating the strengths and signs of the CHD risk associations as determined in the MESA study population of 5677 subjects, 285 of whom suffered a CHD event during 6 years of follow-up (all 9 subpopulations were included in the same logistic regression model, adjusted for age, race, smoking, SBP, hypertension medication, BMI, diabetes, LDL-P and log TG) according to embodiments of the present invention.
Figure 6C:
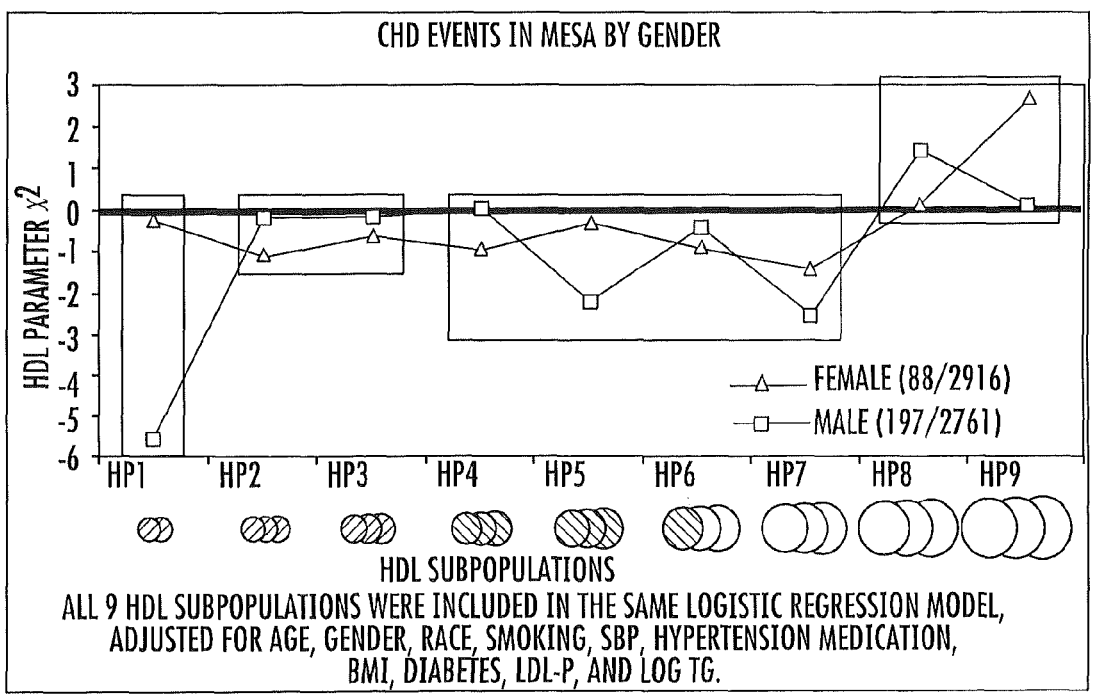
FIG. 6C is a graph showing the same information as in FIG. 6B but showing results separately for the female (88 CHD events among 2916 participants) and male (197 CHD events among 2761 participants) subjects in the MESA study population (all 9 subpopulations were included in the same logistic regression model, adjusted for age, race, smoking, SBP, hypertension medication, BMI, diabetes, LDL-P and log TG).

As shown in FIGS. 6B and 6C, for example, in some embodiments, the total number of subpopulations in the HDL subclasses can be grouped into nine subgroups, HP1-HP9, which can then be further grouped into four groupings shown by the four boxes in FIGS. 6B and 6C. The "four" subclass groupings selected for CHD risk association can be described as $HP_{VS}$ (H1-H2), $HP_S$ (H3-H8), $HP_{ML}$ (H9-20) and $HP_{VL}$ (H21-26). FIG. 6C illustrates the gender differences for the CHD risk relationships of the 9 subgroups and the four groups relative to the "composite" graph shown in FIG. 6B.

Figure 6D:
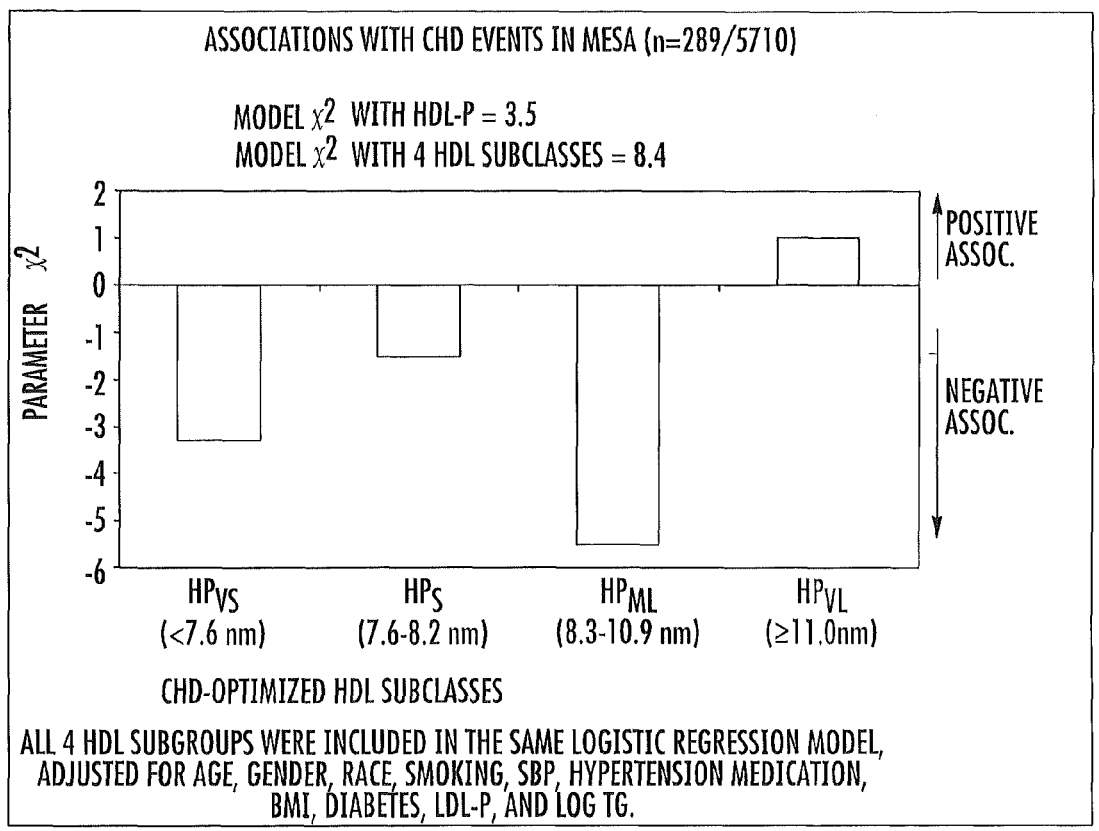
FIG. 6D is a graph of parameter χ2 of CHD events in MESA (n=289/5710) with the 9 subclasses combined into the four boxed HDL subgroups in FIG. 6B (all four HDL subgroups were included in the same logistic regression model, adjusted for age, race, smoking, SBP, hypertension medication, BMI, diabetes, LDL-P and log TG) according to embodiments of the present invention.

FIG. 6D is a graph illustrating risk associations, given by the $\chi 2$ parameter, for each of the four subclass groups $HP_{VS}$, $HP_S$, $HP_{ML}$, $HP_{VL}$. The $HP_S$ subclass association is negative but is closer to a neutral risk association relative to the $HP_{VS}$ or $HP_{ML}$ subclasses. While the HDL risk interaction parameters described herein were configured to exclude $HP_S$, the $HP_S$ subclass could be included as well. However, this can add computational complexity that does not appear warranted based on the risk stratification provided by the other three subclass groups.

FIG. 7 is a chart of the 26 different HDL subpopulations, 9 subgroupings and four subclass groups $HP_{VS}$, $HP_S$, $HP_{ML}$, $HP_{VL}$ which provides the nomenclature and size (average) ranges of the HDL subpopulations according to some embodiments of the present invention. As noted above, the four subclass groups are selected based on a statistical analysis of epidemiologic associations to determine how the various subpopulations should be grouped based on risk association with CHD (rather than LP-IR or insulin resistance or diabetes as described, for example, in U.S. Pat. No. 8,386,187, the content of which is hereby incorporated by reference as if recited in full herein).

FIGS. 8A and 8B are tables illustrating prediction of CHD events in MESA using only data associated with those people having high levels of $HP_{VL}$. The table compares risk prediction given by a base logistic regression model and models also including the different interaction terms, P1, R1, P1+R1 and P1/R1. The base model included the following 10 covariates: age, gender, race, smoking, SBP, hypertension medication, BMI, diabetes, LDL-P and log TG.

FIG. 8A includes data from MESA subjects (n=1145; 42 CHD events) with high concentrations of $HP_{VL}>80^{th}$ percentile (above 1.84 µmol/L).

FIG. 8B includes data from MESA subjects (n=575; 23 CHD events) with even higher concentrations of $HP_{VL}>90\%$ (above 2.71 µmol/L) according to embodiments of the present invention. It is noted that FIG. 8B is provided by way of example only as the relatively small number of events (n=23) make the statistical confidence in the results for the R1 and P1 and interaction components less reliable; additional or larger study populations may improve the reliability of these values.

Figure 8C:
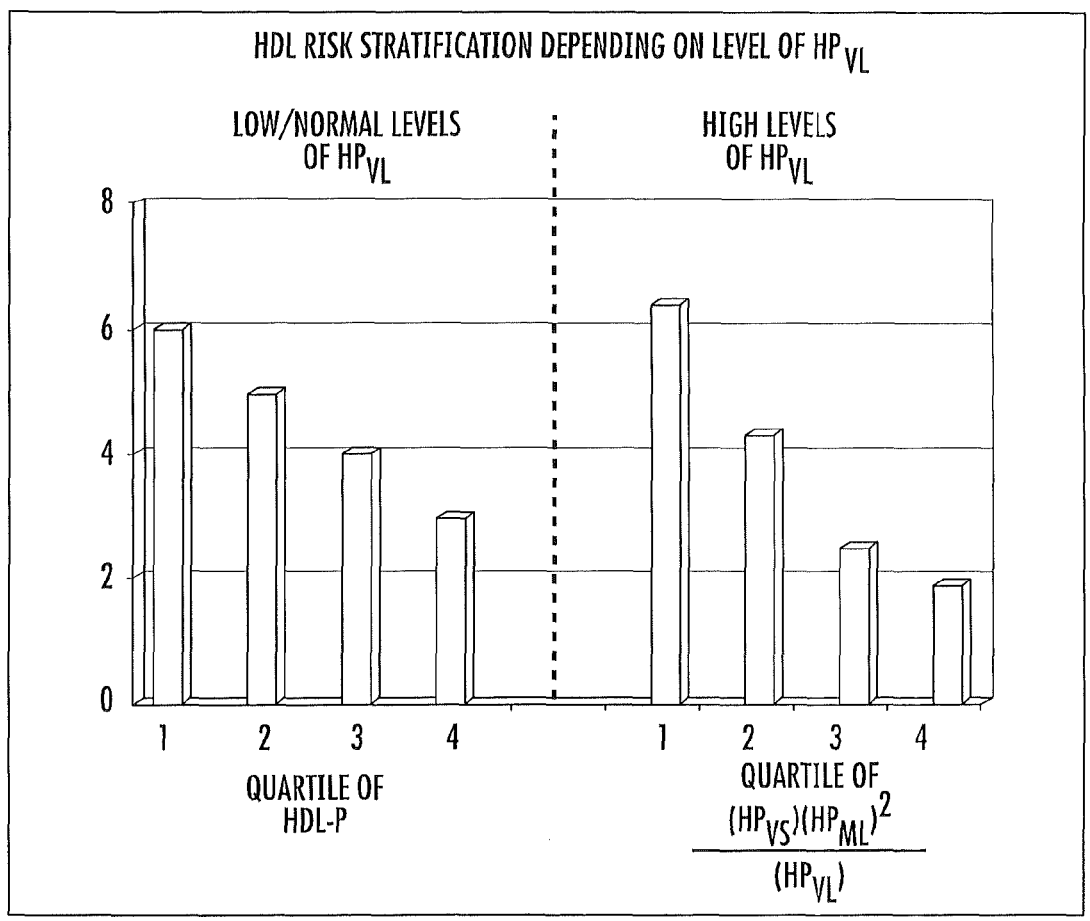
FIG. 8C is a graph illustrating HDL risk stratification based on the level of $HP_{VL}$ according to embodiments of the present invention.

As shown conceptually in FIG. 8C, if the patient's level of $HP_{VL}$ is not high (for example, $<80^{th}$ percentile, or some other appropriate value which may differ from this exemplary threshold), CHD risk can be suitably stratified using quartiles of HDL-P. Alternatively, tertiles, quintiles, or other segmentation of a population can be used. It is also contemplated that instead of HDL-P another NMR HDL parameter could be used such as $(HDL-P)^2$, $HP_{ML}$, or $(HP_{ML})^2$.

On the other hand, if the patient's level of $HP_{VL}$ is high or elevated (e.g., above a defined threshold or range), CHD risk is better (and potentially optimally) stratified by taking account of the relative amounts of three of the four previously discussed subgroups such as those described in FIGS. 8A and 8B: $HP_{VL}$, $HP_{ML}$, and $HP_{VS}$.

In some embodiments, the HDL risk parameter combines P1 and R1 as a ratio, P1/R1.

When combined as P1/R1, the HDL interaction risk parameter is represented by the below equation:

$$(HP_{VS}/HP_{VL})(HP_{ML})^2 \quad \text{Equation (1)}$$

Figure 5:
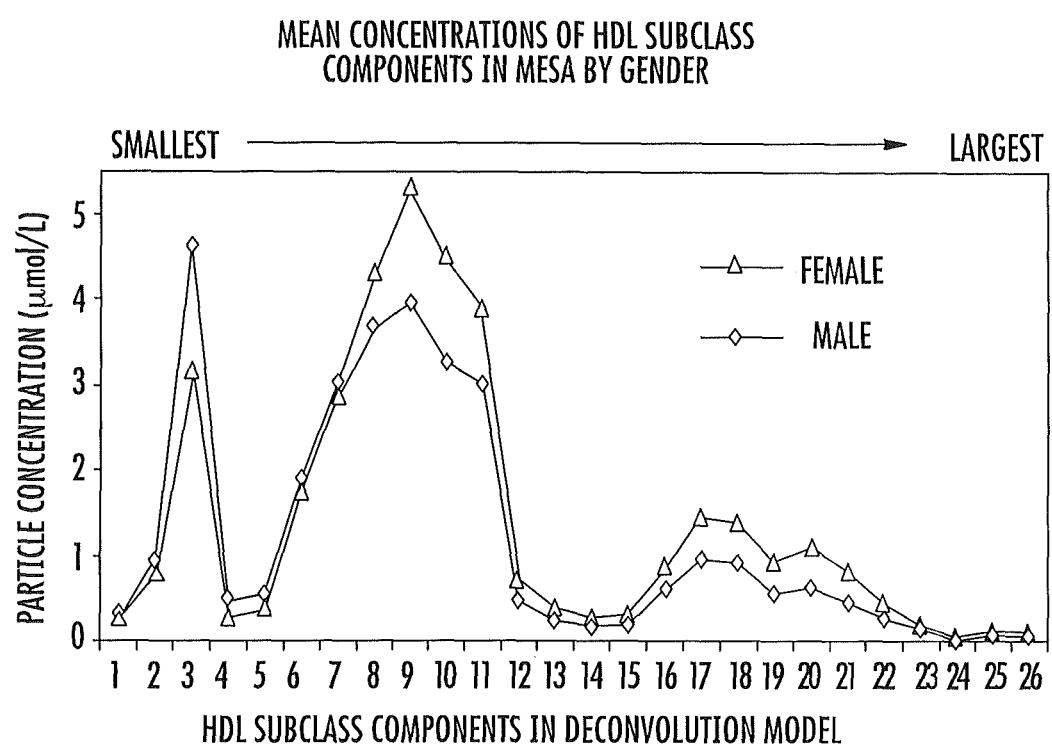
FIG. 5 is a graph showing the mean particle concentrations (µmol/L) of the 26 HDL subclass components from H1 (smallest) to H26 (largest) for men and women in the MESA study population from an exemplary deconvolution model according to embodiments of the present invention.

In this form, the numerator and the denominator of the first term ($HP_{VS}/HP_{VL}$) are both relatively small values (see, FIG. 5) which in a general population may not be sufficiently discriminating (or the denominator may be zero for part of the population) but when directed at the subpopulation of people having high levels of $HP_{VL}$, can be a useful risk predictor.

As shown by the right side of the graph in FIG. 8C, when a person has elevated $HP_{VL}$, the CHD risk may be predicted relative to a combined interaction parameter relative to values associated with a defined segment of the population, e.g., shown as the first quartile or the first and second quartiles (note other population segments can be used, e.g., tertiles, quintiles, and the like) of the HDL interaction parameter such as Equation (1).

Alternative HDL interaction parameters may also or additionally be used such as those shown in FIGS. 8A and 8B, for example.

In some embodiments, the HDL interaction parameter can be as shown in Equation (2) or Equation (3).

$$(HP_{VS})(HP_{ML})/(HP_{VL}) \quad \text{Equation (2)}$$

$$(HP_{ML})^2/(HP_{VL}) \quad \text{Equation (3)}$$

It is contemplated that one or both of the new HDL interaction risk parameter(s) which can include, for example, R1, P1 alone or combined in any manner including the combinations shown in Equations (1)-(3) can be used as a marker for identifying those patients having elevated $HP_{VL}$ that are at increased risk of CHD.

In some embodiments, a respective subject can be identified as at risk for CHD if P1/R1 has a value $\leq 170$ µmol$^2$/L$^2$.

HDL has been associated with a number of different functions including, for example, promoting cholesterol efflux, anti-inflammation, antioxidation, increasing nitrous oxide production, protecting against lipopolysaccharide, vasoprotective, antifibrotic, and anthithrombotic. While the identification may be sufficient to make therapy or risk management decisions on its own, it is contemplated that in some embodiments, additional tests may be carried out on these patients to identify a particular dysfunction(s) to allow for better therapy decisions. Examples of such companion or further assays that may be carried out include, but are not limited to those described in one or more of the following: U.S. Pat. No. 7,723,045 to Fogelman et al., U.S. Pat. No. 7,250,304 to Fogelman et al., U.S. 2011/0124031 to Hazen et al., U.S. Pat. No. 7,771,954 to Hazen et al.; U.S. 2011/0201947 to Hazen et al., U.S. 2010/0285517 to Hazen et al., and U.S. 2005/0244892 to Rader et al., the contents of which are hereby incorporated by reference as if recited in full herein.

Different therapies that increase HDL-C by the same amount may not increase the HDL subclasses proportionately. Some drugs, for example, increase HDL-C mainly by increasing the number of small HDL particles (such as those in the fibrate class). Others increase mainly large HDL-P. The HDL particle subclass concentrations can change differentially with different therapies, indicating potentially greater or lesser clinical benefit and may provide enhanced protocols for evaluating therapeutic efficacy. See, e.g., *Rashedi N, Brennan D, Kastelein J J, Nissen S E, Nicholls S.* 2011 *European Atherosclerosis Society meeting presentation* (providing a graph illustrating the impact of a CETP inhibitor (torceptrapib) on NMR-derived lipoprotein particle parameters.

Embodiments of the invention provide an automated analysis and/or report of a blood or plasma sample of a mammalian patient (typically a human) that identifies a likelihood of increased CHD risk for patients having high levels of $HD_{VL}$. An HDL therapy can be adjusted, monitored or selected based on the CHD risk identification. Thus, the CHD risk using the HDL interaction risk parameter (e.g., R1 and/or P1) when a patient has elevated very large HDL-P may can be used as a risk assessment and/or therapy management tool.

Figure 10A:
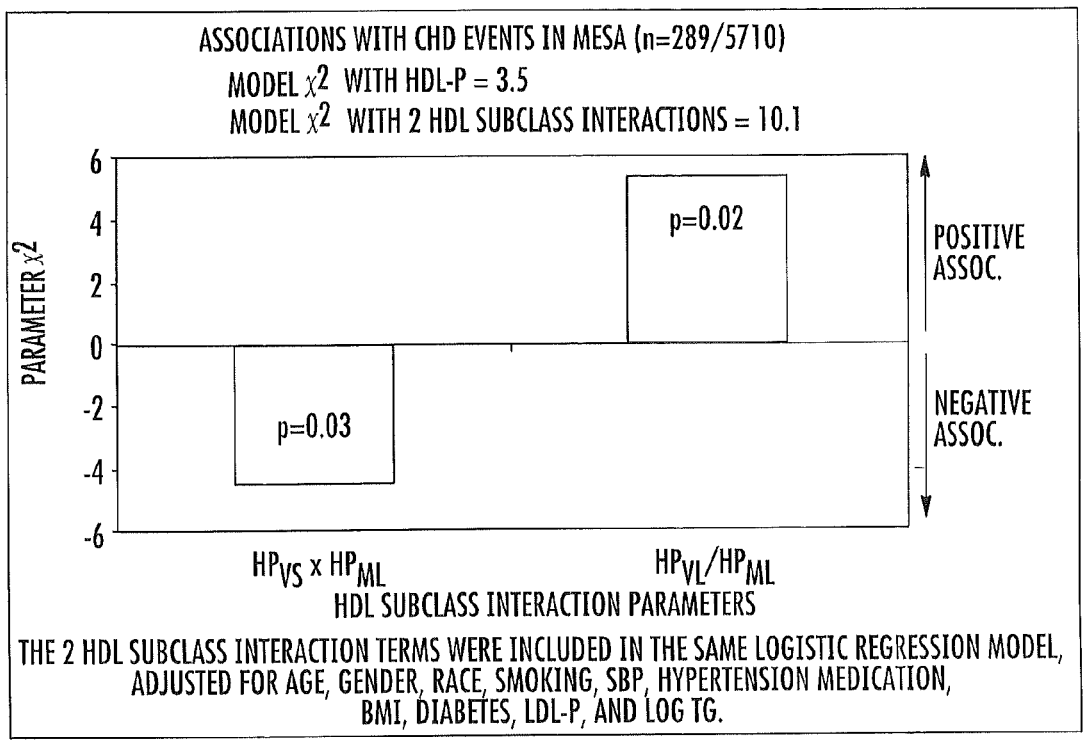
FIG. 10A is a graph showing associations with CHD events in MESA (n=289/5710), given by the parameter $\chi 2$ value, for the two interaction variables, P1: $(HP_{VS} \times HP_{ML})$ and R1: $(HP_{VL}/HP_{ML})$, with the former having a negative risk relationship and the latter a positive risk relationship. Results are from a logistic regression model including both HDL interaction parameters, adjusted for age, gender, race, smoking, SBP, hypertension medication, BMI, diabetes, LDL-P and log TG) according to embodiments of the present invention.

FIG. 10A is a graph of parameter $\chi 2$ showing associations of CHD events in MESA (n=289/5710) for P1 ($HP_{VS} \times HP_{ML}$) and R1 ($HP_{VL}/HP_{ML}$) HDL interaction risk components (one having a positive risk association and one having a negative risk association) included in the same logistic regression model, adjusted for age, gender, race, smoking, SBP, hypertension medication, BMI, diabetes, LDL-P and log TG according to embodiments of the present invention. The model $\chi 2$ increased more than double with two subclass interactions.

Figure 10B:
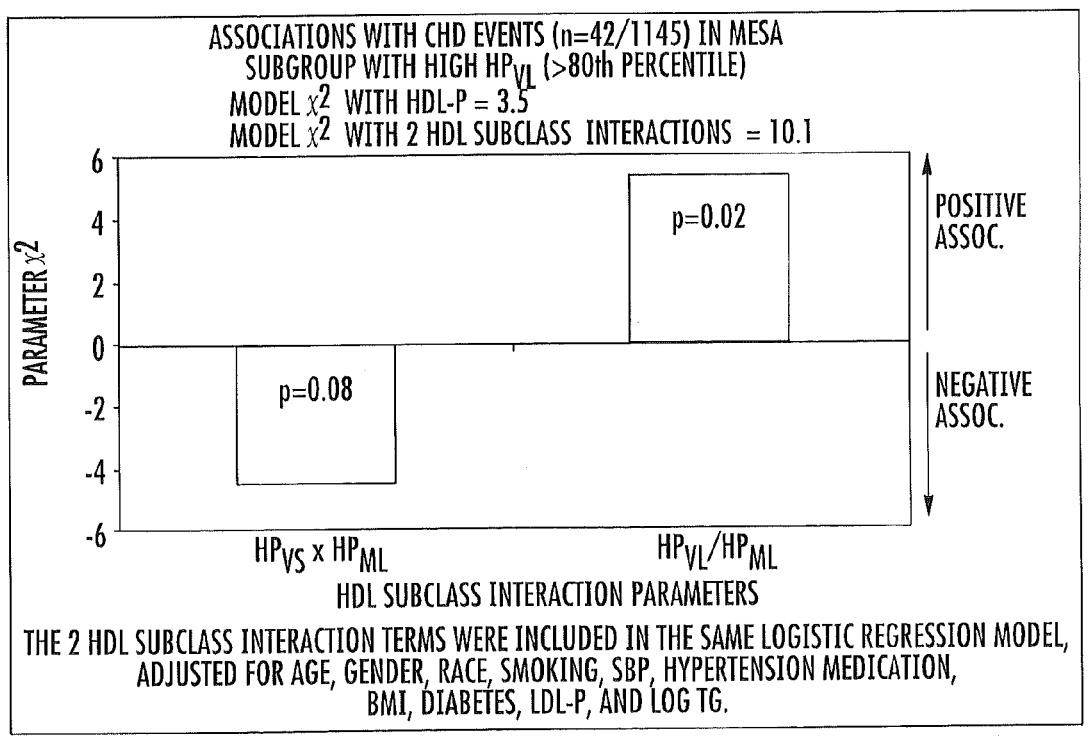
FIG. 10B is a graph showing the same information as in FIG. 10A, but with analysis restricted to the subgroup of individuals (n=42/1145) having elevated concentrations (above the 80$^{th}$ percentile; >1.84 μmol/L) of very large HDL particles, H21-H26, according to embodiments of the present invention.

FIG. 10B is a graph of parameter $\chi 2$ showing associations of CHD events in MESA (n=42/1145) in a population subgroup having high $HP_{VL}$ for P1 ($HP_{VS} \times HP_{ML}$) and R1 ($HP_{VL}/HP_{ML}$). This graph is similar to that shown in FIG. 10A. As for FIG. 10A, the P1 HDL interaction component has negative association and the R1 interaction component has a positive risk association with CHD. The two HDL interaction parameters or terms were included in the same logistic regression model, adjusted for age, gender, race, smoking, SBP, hypertension medication, BMI, diabetes, LDL-P and log TG) according to embodiments of the present invention.

Figure 11:
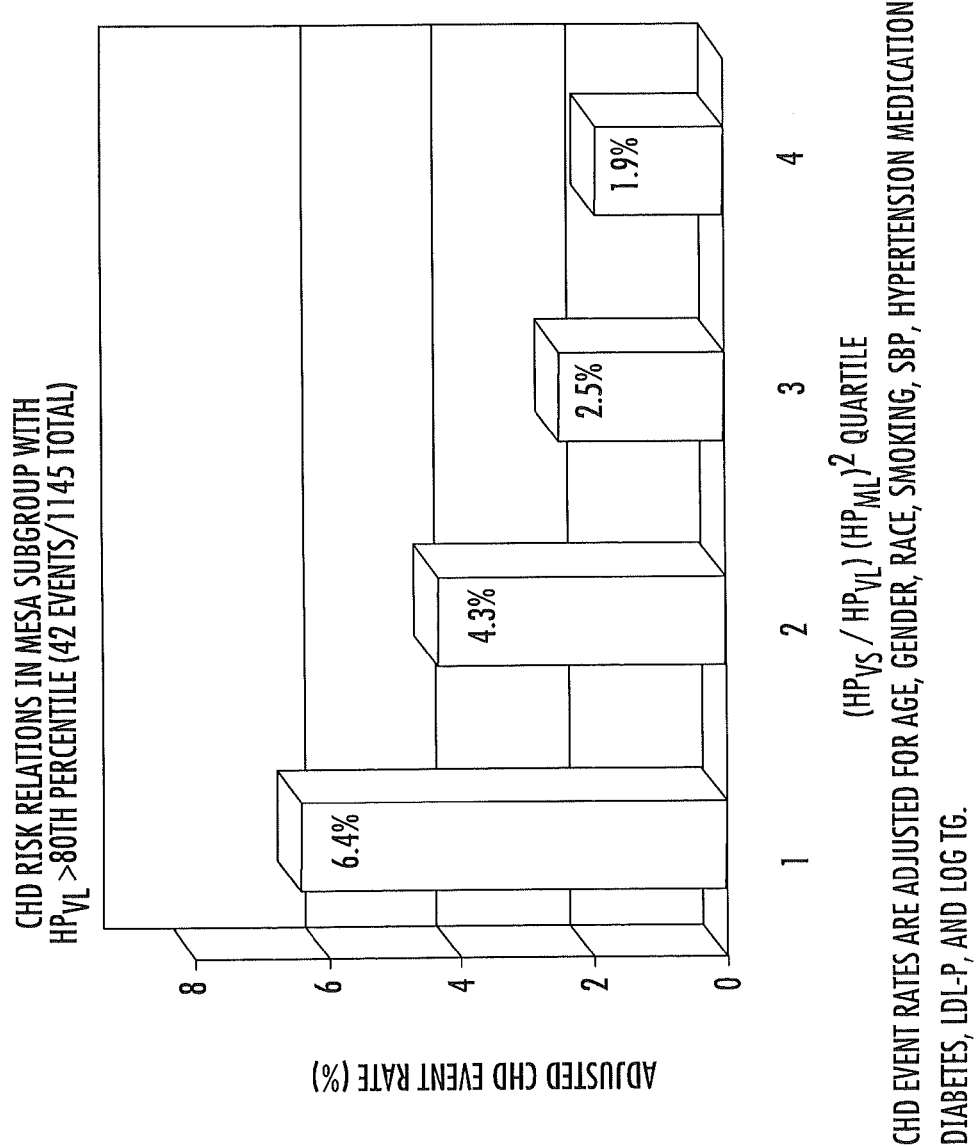
FIG. 11 is a graph showing the CHD event rate (%), adjusted for age, gender, race, smoking, SBP, hypertension medication, BMI, diabetes, LDL-P and log TG, by quartile of the P1/R1 ratio (which is equal to $(HP_{VS}/HP_{VL})(HP_{ML})^2$) in MESA subjects (n=42/1145) having $HP_{VL}$>80$^{th}$ percentile according to embodiments of the present invention.

FIG. 11 is a graph showing the adjusted CHD event rates of individuals divided into quartiles according to the P1/R1 ratio in MESA subjects (n=42/1145) having $HP_{VL}>80^{th}$ percentile according to embodiments of the present invention.

Figure 12:
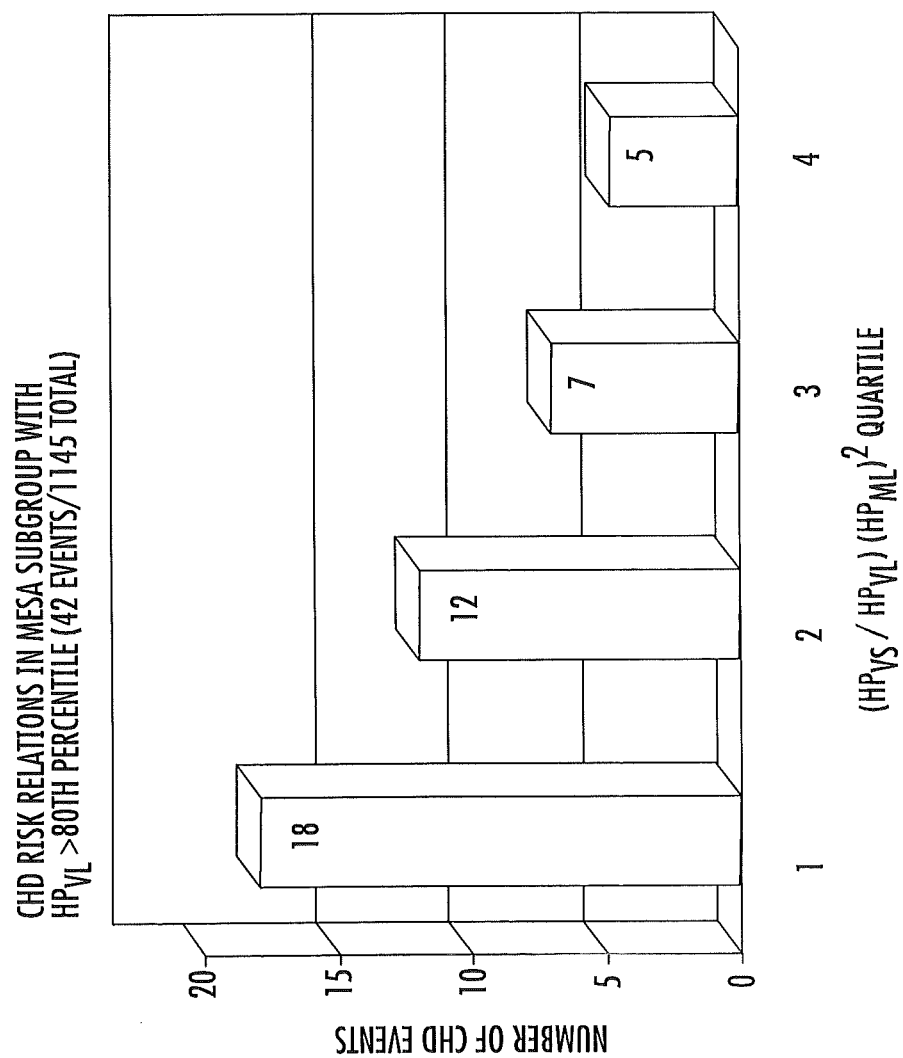
FIG. 12 is a graph similar to that shown in FIG. 11 showing the number of CHD events by quartile of the P1/R1 ratio in MESA subjects (n=42/1145) having $HP_{VL}$>80$^{th}$ percentile according to embodiments of the present invention.

FIG. 12 is a graph similar to that shown in FIG. 11 showing the numbers $80^{th}$ of CHD events in each P1/R1 quartile in MESA subjects (n=42/1145) having $HP_{VL}>80^{th}$ percentile according to embodiments of the present invention.

Figure 13:
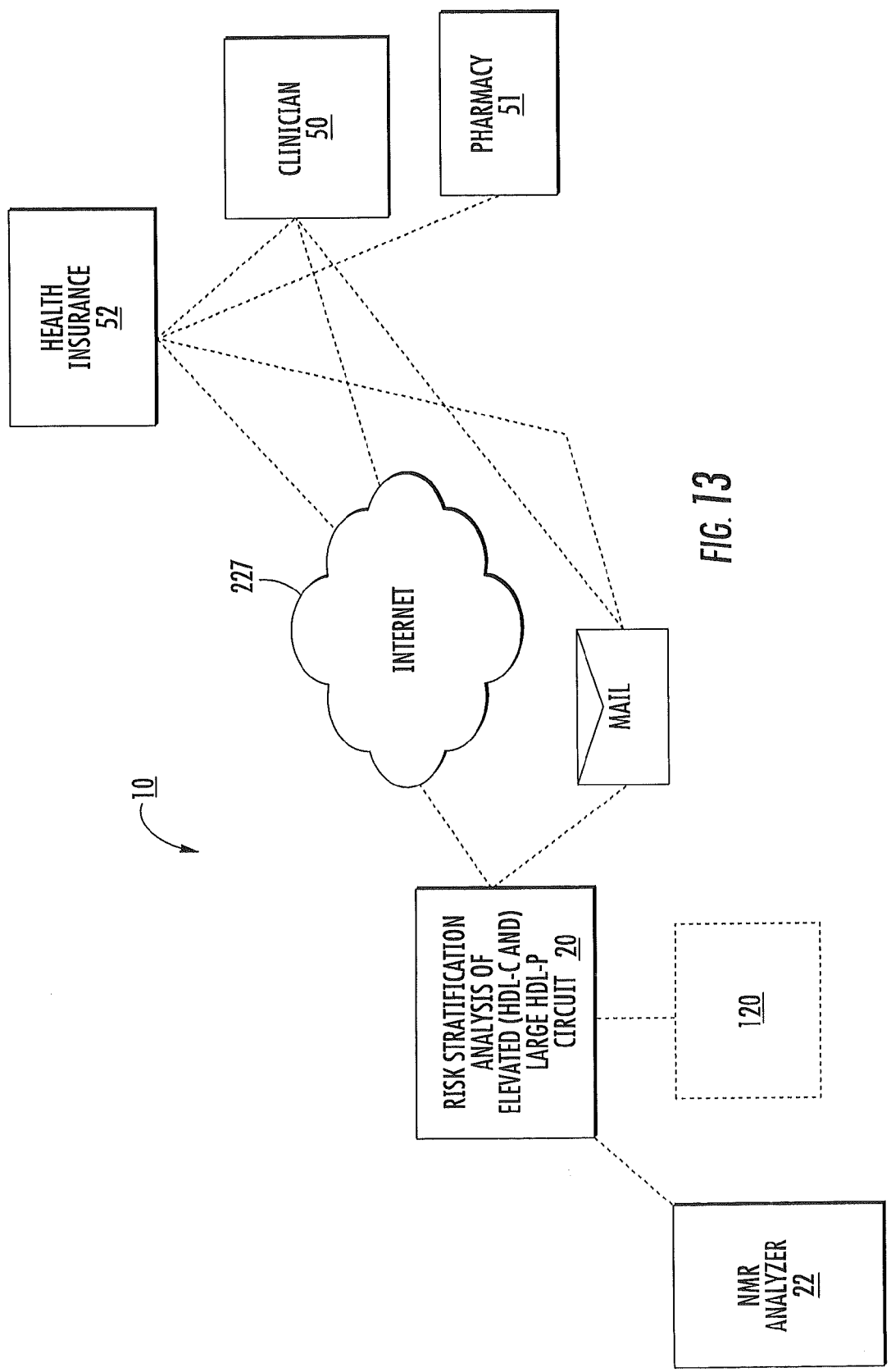
FIG. 13 is a schematic illustration of a system for analyzing CHD risk using a defined risk parameter comprising a subclass grouping of large HDL-P (H21-26) according to embodiments of the present invention.

Referring now to FIG. 13, it is contemplated that the protective (and optionally non-protective) HDL-P analysis can be carried out using a system 10 with an NMR clinical analyzer 22 as described, for example, with respect to FIG. 14 below and/or in U.S. Pat. No. 8,013,602, the contents of which are hereby incorporated by reference as if recited in full herein.

The system 10 can include a CHD risk analysis circuit for elevated large HDL-P 20 that can be on-board the analyzer 22 or remote from the analyzer 22. If the latter, the analysis module or circuit 20 can reside totally or partially on a server 150. The server 150 can be provided using cloud computing which includes the provision of computational resources on demand via a computer network. The resources can be embodied as various infrastructure services (e.g. compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increase risk of an adverse event. The results can be sent to a patient via email to a "home" computer or to a pervasive computing device such as a smart phone or notepad and the like. The results can be as an email attachment of the overall report or as a text message alert, for example.

Figure 14:
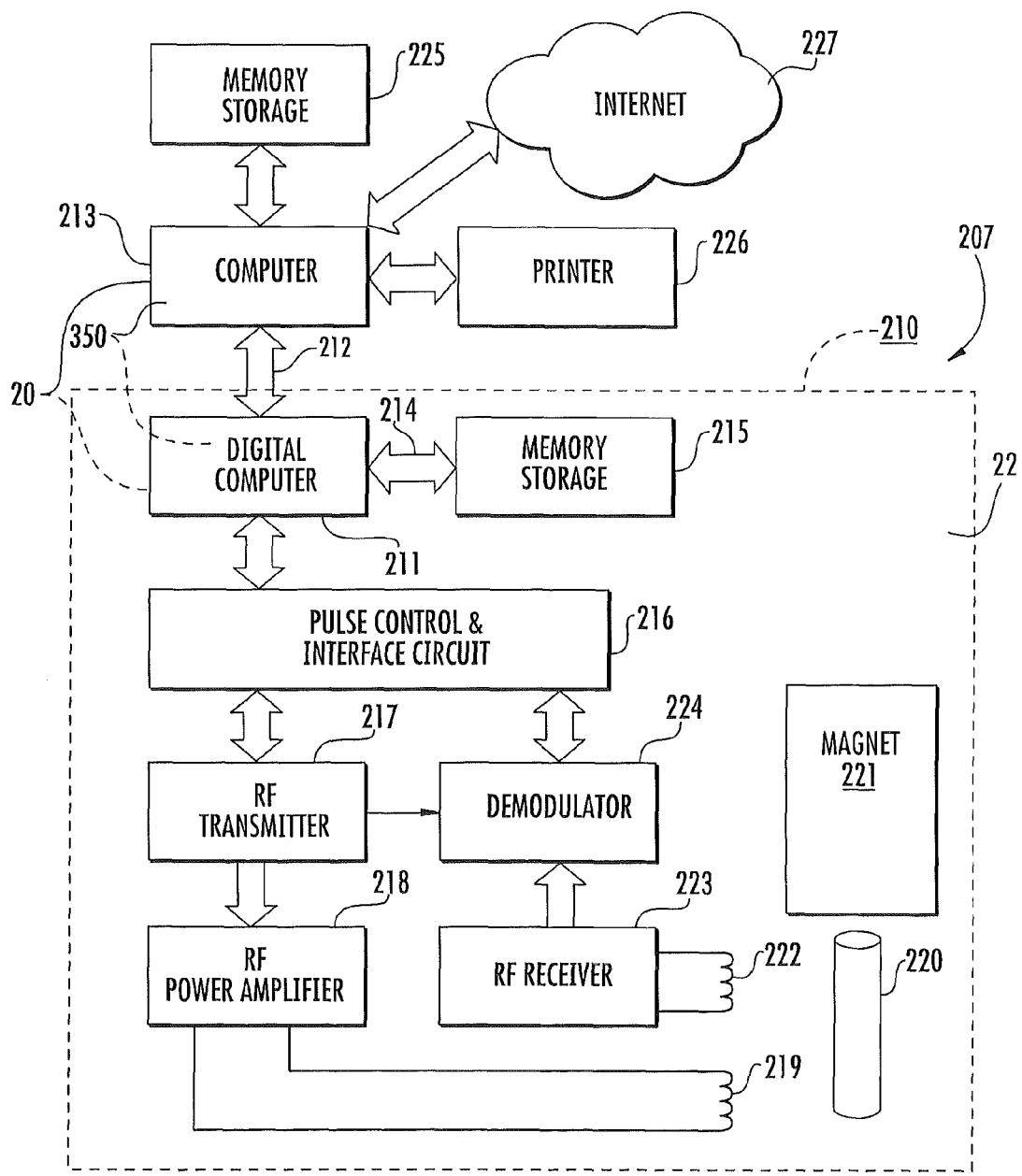
FIG. 14 is a schematic illustration of a NMR spectroscopy apparatus according to embodiments of the present invention.

Referring now to FIG. 14, a system 207 for acquiring and calculating the lineshape of a selected sample is illustrated. The system 207 includes an NMR spectrometer 22 for taking NMR measurements of a sample. In one embodiment, the spectrometer 22 is configured so that the NMR measurements are conducted at 400 MHz for proton signals; in other embodiments the measurements may be carried out at 360 MHz or other suitable frequency. Other frequencies corresponding to a desired operational magnetic field strength may also be employed, typically between about 200 MHz-900 MHz. Typically, a proton flow probe is installed, as is a temperature controller to maintain the sample temperature at 47+/−0.5 degrees C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The lipoprotein measurement and/or protective HDL-P analyzer circuit 20 or module 350 (FIGS. 13-15) or circuit 20 can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory, the computer 213, which may be a personal, laptop, desktop, workstation, notepad or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that evaluate elevated levels of large HDL-P numbers to identify those people at an increased risk of having or developing CHD that may be particularly useful in automated screening tests and/or risk assessment evaluations for CHD screening of in vitro biosamples.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 15:
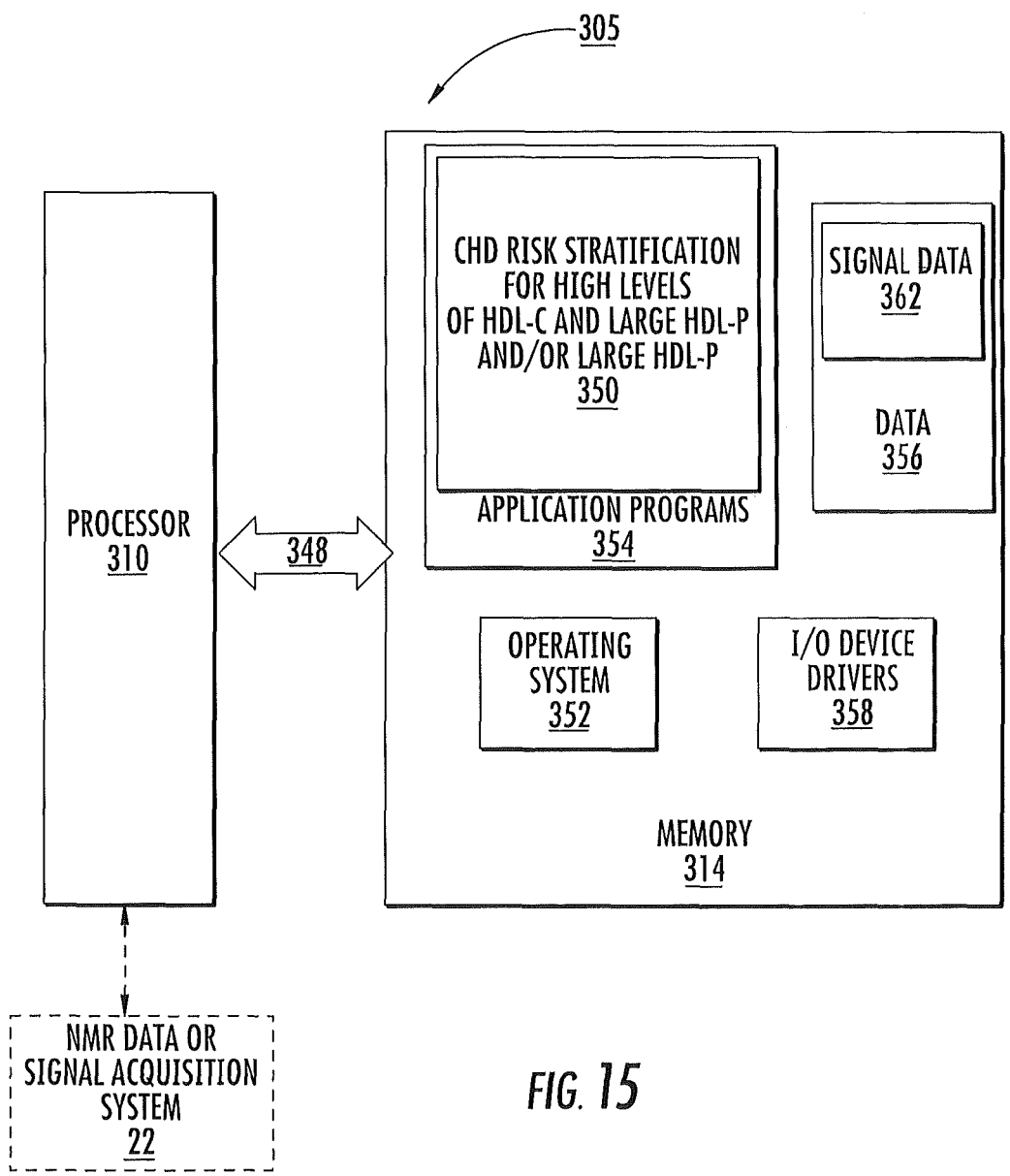
FIG. 15 is a schematic diagram of a data processing system according to embodiments of the present invention.

FIG. 15 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 15, the memory 314 may include several categories of software and data used in the data processing system 305: the operating system 352; the application programs 354; the input/output (I/O) device drivers 358; a CHD risk stratification for High Levels of $HP_{VL}$ Module 350; and the data 356. The Module 350 can sum concentrations of defined subpopulations of HDL to determine if an elevated HPVL condition exits then calculate an HDL interaction risk parameter using different defined subpopulations of the HDL.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 15, as will be appreciated by those of skill in the art, other configurations may also be utilized while still benefiting from the teachings of the present invention. For example, the protective HDL-P Module 350 may also be incorporated into the operating system 352, the I/O device drivers 358 or other such logical division of the data processing system 305. Thus, the present invention should not be construed as limited to the configuration of FIG. 15, which is intended to encompass any configuration capable of carrying out the operations described herein.

In certain embodiments, the Module 350 includes computer program may be used to indicate whether therapy intervention is desired and/or track efficacy of a therapy.

Figure 16:
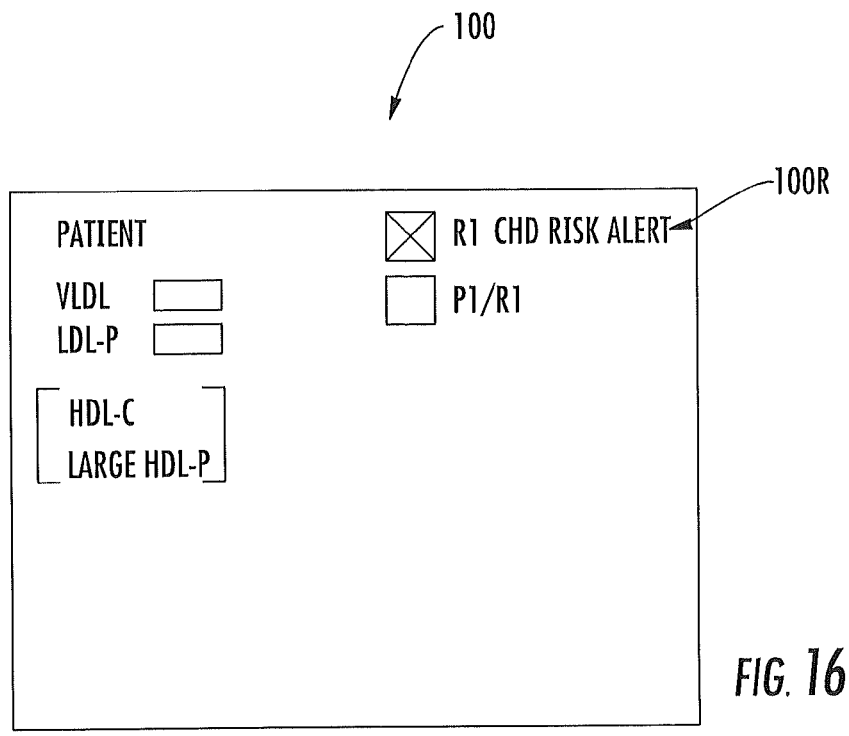
FIG. 16 is an example of a patient report that includes a protective HDL-P number according to embodiments of the present invention.

FIG. 16 is a schematic illustration of an exemplary patient test report 100 that can include various lipoprotein parameters such as LDL-P, VLDL and a CHD risk alert 100R based on a calculated HDL interaction risk parameter (shown as both R1 and P1/R1 for example) when a patient has elevated concentrations of (very) large HDL-P. The HDL interaction risk number can be presented with a risk assessment data correlated to population norms, typical ranges, and/or degree of risk.

Figure 17A:
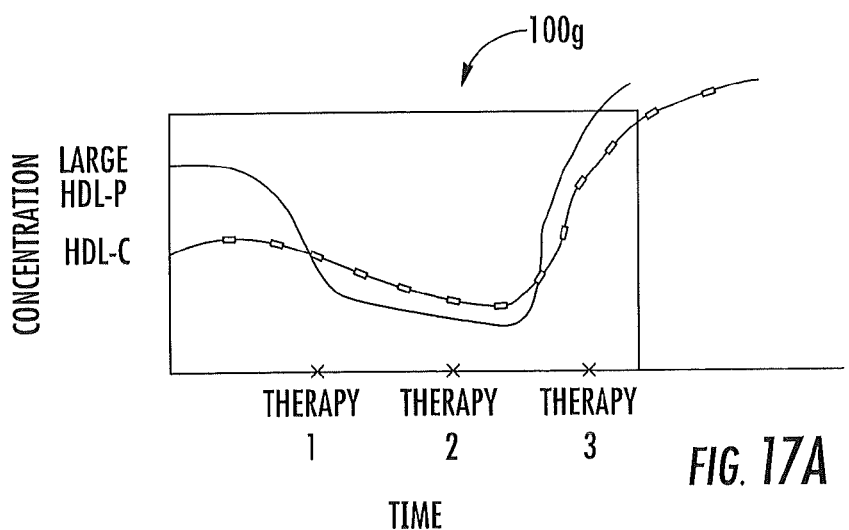
FIGS. 17A and 17B are examples of graphs that can monitor change in one or more of very large HDL-P, R1, P1, R1+P1, P1/R1 or R1/P1 and/or HDL-C over time to evaluate a patient's metabolic status, change, or clinical efficacy of a therapy or even used for clinical trials and the like according to embodiments of the present invention.

FIG. 17A illustrates that a graph of various HDL parameters can be generated including, for example, one or more of (very) large HDL-P, HDL-C, protective and NP HDL-P can be provided to illustrate a change in patient metabolic HDL function over time due to age, medical intervention or a therapy according to some embodiments.

Figure 17B:
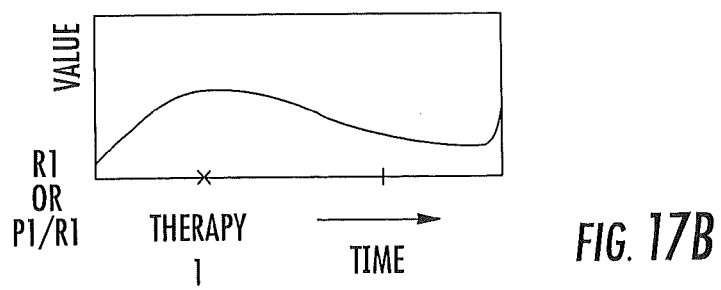

As shown in FIG. 17B, R1 and/or P1/R1 (or another HDL risk interaction) along with the level of $HP_{VL}$ can be tracked using a graph or data over time to monitor a patient over time to correlate known start or use of a drug or other therapy and/or to evaluate whether HDL function has been altered and/or whether protective (or non-protective) HDL-P has been increased or decreased using such therapy.

Tracking of one or more of these parameters may provide better clinical indicators of efficacy of a therapy and/or a better risk predictor for CHD for patients.

Future drugs or uses of known drugs can be identified, screened or tested in patients identified using the HDL-P evaluations.

Figure 18:
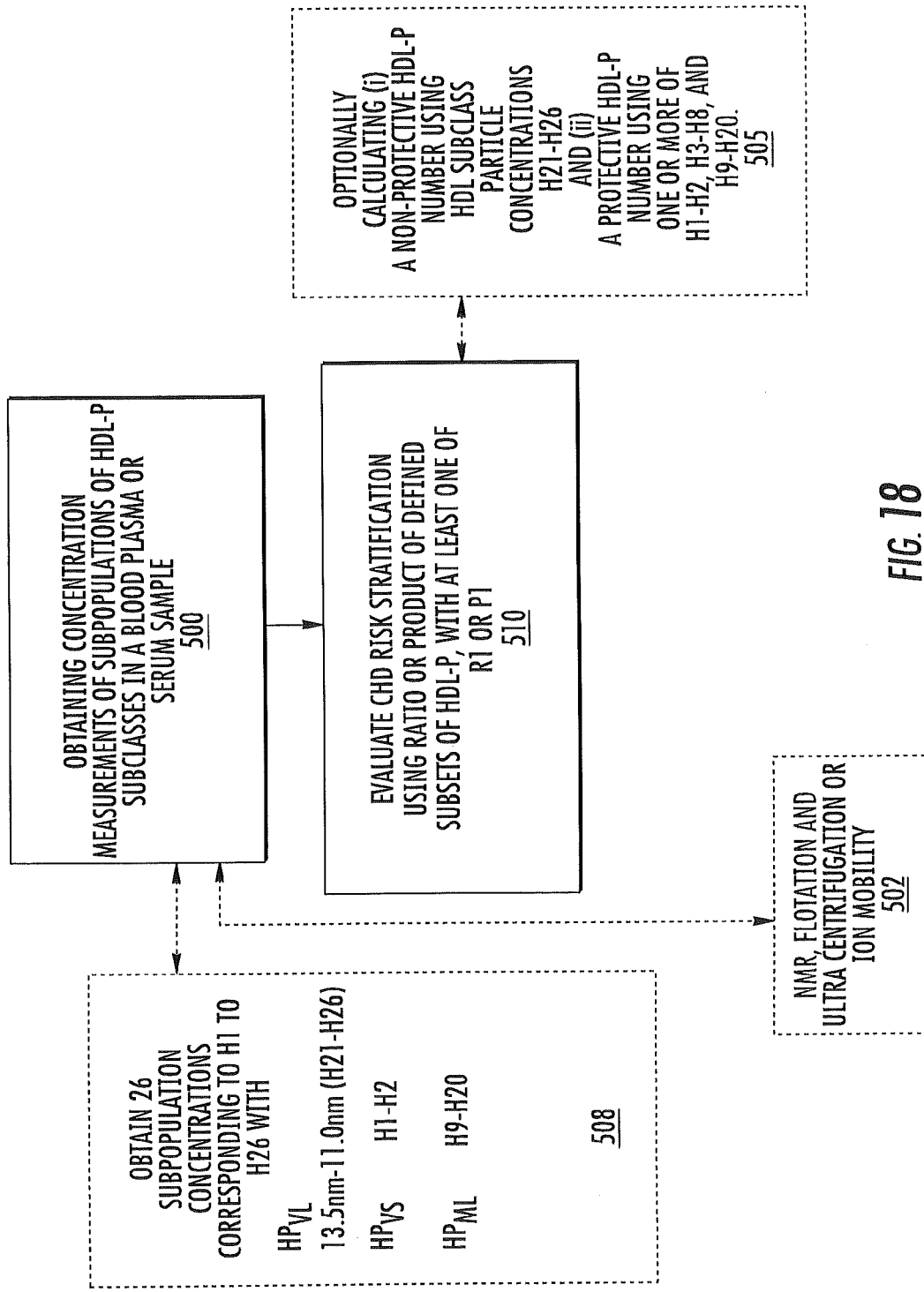
FIG. 18 is a flow chart of exemplary operations that can be used to carry out embodiments of the present invention.

FIG. 18 is a flow chart of exemplary operations that can be used to carry out embodiments of the invention for determining protective high density lipoprotein particle (HDL-P) numbers. Concentration measurements of subpopulations of HDL-P subclasses in a blood plasma or serum sample can be obtained (block 500). The number of subpopulations can vary but typically include at least 20, such as about 26. CHD risk stratification can be evaluated using a ratio or product of defined subsets of the HDL subpopulations, e.g., at least one of R1 or P1 (block 510).

The concentrations can be via NMR, flotation and ultracentrifugation or ion mobility, for example (block 502).

Twenty six subpopulation concentrations can be obtained, corresponding to H1 to H26, where $HP_{VL}$=H21-26 (e.g., particles within about 14 nm or 13.5 nm to 11 nm), $HP_{VS}$=H1+H2 (e.g., particles within about 7.4 nm-7.5 nm), and $HP_{ML}$=H9-H20 (particles within about 8.3-10.9 nm) (block 508).

Optionally, a CHD risk based non-protective HDL number (H21-H26) and/or a protective HDL number can be calculated using one or more of: H1-H2, H-3-H8, and H-9-H20) (block 505).

It is contemplated that there can be at least two different defined CHD risk tests, one for those people with low or normal levels of very large HDL-P ($HP_{VL}$) and one for those with elevated levels of very large HDL-P ($HP_{VL}$). The former can use the HDL-P number while the latter can have a modified test that considers the HDL risk interaction parameter.

In other embodiments, a standard test can be performed on all samples and a secondary test on those with the elevated very large HDL-P ($HP_{VL}$).

For laboratories performing only HDL-C, where a person has high levels of HDL-C, they can be referred or a sample processed to see if there are elevated levels of very large HDL-P ($HP_{VL}$).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining whether a subject with elevated concentrations of very large high density lipoprotein (HDL) particles (HDL-P) is at increased risk for a cardiac event and/or CHD, comprising:
   providing a blood plasma or serum sample from the subject;
   measuring, using a NMR spectrometer;
   $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$, is a concentration of very large HDL-P subclasses,
   programmatically calculating at least one HDL interaction risk parameter associated with HDL content of the blood plasma or serum sample of the subject, the at least one HDL interaction risk parameter comprising P1 or R1, or P1 and R1, wherein P1 is a product defined by $HP_{VS}$ times $HP_{ML}$, and wherein R1 is a ratio defined by $HP_{VL}/HP_{ML}$, and
   determining the risk for a cardiac event and/or CHD using the at least one HDL interaction risk parameter.

2. The method of claim 1, wherein the at least one HDL interaction risk parameter is at least one of the following: $(HP_{VS})(HP_{ML})/(HP_{VL})$, or $((HP_{VS})(HP_{ML})^2)/(HP_{VL})$, or $(HP_{ML})^2/(HP_{VL})$.

3. The method of claim 1, further comprising: electronically identifying when a subject has an elevated concentration of very large HDL-P ($HP_{VL}$) relative to a population norm, wherein the subject has an elevated concentration of $HP_{VL}$ when the subject's concentration is ≥80% of a population norm, and wherein the programmatic calculation of at least one HDL interaction risk parameter is electronically selectively carried out only when the subject has the elevated concentration of $HP_{VL}$.

4. The method of claim 1, wherein the $HP_{VS}$ includes HDL subpopulations having an average diameter between 7.4 nm and 7.6 nm.

5. The method of claim 1, wherein the $HP_{ML}$ includes HDL subpopulations having an average diameter between 8.3 nm and 10.9 nm.

6. The method of claim 1, wherein the $HP_{VL}$ includes HDL subpopulations having an average diameter between 11 nm and 13.5 nm.

7. The method of claim 1, further comprising:
   deconvolving an NMR composite signal into 26 subpopulations (H1-H26) of different sizes of HDL-P ranging from a smallest HDL-P size associated with H1 to a largest HDL-P size associated with H26;
   electronically calculating concentrations of H1 and H2 to generate the $HP_{VS}$;
   electronically calculating concentrations of H9-H20 to generate the $HP_{ML}$; and electronically calculating concentrations of H21 and H26 to generate the $HP_{VL}$.

8. The method of claim 1, wherein the programmatically calculated at least one HDL interaction risk parameter includes P1/R1.

9. The method of claim 8, wherein a subject is identified as at risk for CHD if P1/R1 for the subject has a value in the first or second quartile of a population norm.

10. The method of claim 8, wherein a subject is identified as at risk for CHD if P1/R1 for the subject has a value ≤170 $\mu mol^2/L^2$.

11. The method of claim 1, further comprising generating a report that visually and/or textually indicates whether the subject is at increased risk of CHD despite having elevated $HP_{VL}$.

12. The method of claim 1, further comprising generating a report based on the programmatic calculation of the at least one HDL interaction risk parameter that includes at least one of the following: R1, P1, P1/R1, or P1+R1.

13. The method of claim 1, further comprising electronically monitoring whether there is a change in the HDL risk interaction parameter over time to assess a change in CHD risk when $HP_{VL}$ remains above 1.84 µmol/L.

14. The method of claim 1, further comprising referring the subject for further medical evaluation if the programmatic calculation indicates there is a likelihood of increased risk of CHD despite an elevated very large HDL-P.

15. The method of claim 1, wherein the subject is mammalian and wherein the obtaining and calculating steps are carried out using at least one processor, the method further comprising providing a report indicating whether the subject is at risk of having and/or developing CHD based, in part, on the programmatic calculation.

16. The method of claim 1, further comprising monitoring the at least one HDL interaction risk parameter for a change in the HDL risk interaction parameter over time.

17. The method of claim 16, wherein the monitoring comprises a computer program used to indicate whether therapy intervention is desired and/or track efficacy of a therapy.

18. A method of determining whether a subject is at increased risk for a cardiac event and/or CHD, comprising:
(a) providing a blood plasma or serum sample from the subject, wherein the subject has elevated high density lipoprotein-cholesterol (HDL-C) that is at least one of: ≥60 mg/dL, ≥80 mg/dL, or ≥100 mg/dL;
(b) measuring by a NMR spectrometer concentrations for $HP_{VS}$, $HP_{ML}$ and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses,
(c) electronically identifying whether the subject also has an elevated concentration of $HP_{VL}$ that is ≥80% of a population norm,
(d) programmatically calculating at least one HDL interaction risk parameter associated with HDL content of the blood plasma or serum sample of the subject, the at least one HDL interaction risk parameter comprising at least two of $HP_{VS}$, $HP_{ML}$, and $HP_{VL}$ if the subject has the elevated concentration of $HP_{VL}$ that is ≥80% of a population norm, and
(e) determining whether the subject is at increased risk using the at least one HDL interaction risk parameter.

19. A computer program product for stratifying CHD risk for patients with elevated concentrations of very large high density lipoprotein (HDL) particles (HDL-P), the computer program product comprising: a non-transitory computer readable storage medium having computer readable program code embodied in the medium, the computer-readable program code comprising:
computer readable program code that obtains NMR signal data of an in vitro blood plasma or serum sample of a subject to determine NMR-derived concentration measurements of at least twenty subpopulations of HDL-P subclasses in a blood plasma or serum sample;
computer readable program code for electronically identifying when the subject has an elevated concentration of $HP_{VL}$ relative to a population norm, wherein the subject has an elevated concentration of $HP_{VL}$ when the subject's $HP_{VL}$ concentration is ≥80% of a population norm; and
computer readable program code that calculates at least one HDL interaction risk parameter associated with HDL content of a blood plasma or serum sample of the subject, the at least one HDL interaction risk parameter comprising at least two of $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses, wherein the at least one HDL interaction risk parameter includes P1 or R1, or P1 and R1, wherein P1 is a product defined by $HP_{VS} \times HP_{ML}$, and wherein R1 is a ratio defined by $HP_{VL}/HP_{ML}$, and
computer readable program code that determines the risk of CHD for the subject using the at least one HDL interaction risk parameter.

20. The computer program product of claim 19, further comprising computer readable program code that screens subjects that may benefit from an HDL risk stratification test by (a) first identifying if the subject has elevated high density lipoprotein-cholesterol (HDL-C) that is at least one of: ≥60 mg/dL, ≥80 mg/dL, or ≥100 mg/dL; then (b) identifying when the subject also has an elevated concentration of $HP_{VL}$ that is ≥80% of a population norm, then directing the calculation if the subject has the elevated concentration of $HP_{VL}$.

21. The computer program product of claim 19, wherein the $HP_{VS}$ includes HDL subpopulations having an average diameter between 7.4 nm and 7.6 nm, wherein the $HP_{ML}$ includes HDL subpopulations having an average diameter between 8.3 nm and 10.9 nm, and wherein the $HP_{VL}$ includes HDL subpopulations having an average diameter between 11 nm and 13.5 nm.

22. The computer program product of claim 19, further comprising computer readable program code configured to:
deconvolve an NMR composite signal into 26 subpopulations (H1-H26) of different sizes of HDL-P ranging from a smallest HDL-P size associated with H1 to a largest HDL-P size associated with H26;
calculate concentrations of H1 and H2 to generate the $HP_{VS}$;
calculate concentrations of H9-H20 to generate the $HP_{ML}$; and
calculate concentrations of H21 and H26 to generate the $HP_{VL}$.

23. The computer program product of claim 19, wherein the at least one HDL interaction risk parameter includes P1/R1.

24. The computer program product of claim 23, wherein the subject is identified as at risk for CHD if P1/R1 has a value in the first or second quartile of a population norm.

25. The computer program product of claim 23, wherein the subject is identified as at risk for CHD if P1/R1 has a value ≤170 μmol$^2$/L$^2$.

26. The computer program product of claim 19, further comprising generating a report that visually and/or textually indicates whether the subject is at increased risk of CHD despite having elevated $HP_{VL}$.

27. The computer program product of claim 19, further comprising computer readable program code configured to electronically provide data representing, generate a graph showing, and/or monitor whether there is a change in the HDL risk interaction parameter for the subject over time to assess a change in CHD risk when $HP_{VL}$ remains above 1.84 μmol/L.

28. The computer program product of claim 19, wherein the subject is mammalian, the product further comprising computer readable program code that obtains NMR signal data of an in vitro blood plasma or serum sample of the subject to determine NMR derived concentration measurements, and computer readable code that provides a report indicating whether the subject is at risk of having and/or developing CHD based, in part, on the at least one HDL interaction risk parameter.

29. A system for analyzing CHD risk, comprising: a circuit comprising at least one processor configured to determine whether a subject with elevated concentrations of very large high density lipoprotein (HDL) particles (HDL-P) is at increased risk for a cardiac event and/or CHD, the at least one processor configured to
obtain NMR signal data of an in vitro blood plasma or serum sample of the subject,
determine NMR-derived concentration measurements for $HP_{VS}$, $HP_{ML}$, and $HP_{VL}$, where $HP_{VS}$ is a concentration of very small HDL-P subclasses, $HP_{ML}$ is a concentration of medium and large HDL-P subclasses, and $HP_{VL}$ is a concentration of very large HDL-P subclasses, and
calculate at least one HDL interaction risk parameter associated with HDL content of a blood plasma or serum sample of the subject, the at least one HDL interaction risk parameter comprising P1 or R1, or P1 and R1, wherein P1 is a product defined by $HP_{VS}$ times $HP_{ML}$, and wherein R1 is a ratio defined by $HP_{VL}/HP_{ML}$.

30. The system of claim 29, wherein the circuit is onboard or in communication with an NMR spectrometer for acquiring at least one NMR spectrum of an in vitro blood plasma or serum sample.

31. The system of claim 29, wherein the at least one processor is configured to identify when a subject has an elevated concentration of $HP_{VL}$ relative to a population norm, wherein the subject has an elevated concentration of $HP_{VL}$ when the subject's $HP_{VL}$ concentration is ≥80% of a population norm, and wherein the at least one processor is configured to provide a CHD risk assessment using the at least one HDL interaction risk parameter only when the subject has the elevated concentration of $HP_{VL}$.

32. The system of claim 29, wherein the at least one processor is configured to screen subjects that may benefit from an HDL risk stratification test by (a) first identifying if the subject has elevated high density lipoprotein-cholesterol (HDL-C) that is at least one of: ≥60 mg/dL, ≥80 mg/dL, or ≥100 mg/dL; then (b) identifying when the subject also has an elevated concentration of $HP_{VL}$ that is ≥80% of a population norm.

33. The system of claim 29, wherein the $HP_{VS}$ includes HDL subpopulations having an average diameter between 7.4 nm and 7.6 nm, wherein the $HP_{ML}$ includes HDL subpopulations having an average diameter between 8.3 nm and 10.9 nm, and wherein the $HP_{VL}$ includes HDL subpopulations having an average diameter between 11 nm and 13.5 nm.

34. The system of claim 29, wherein the at least one processor is configured to deconvolve an NMR composite signal into 26 subpopulations (H1-H26) of different sizes of HDL-P ranging from a smallest HDL-P size associated with H1 to a largest HDL-P size associated with H26, then:
calculate concentrations of H1 and H2 to generate the $HP_{VS}$;
calculate concentrations of H9-H20 to generate the $HP_{ML}$; and
calculate concentrations of H21 and H26 to generate the $HP_{VL}$.

35. The system of claim 29, wherein the at least one HDL interaction risk parameter includes P1/R1.

36. The system of claim 35, wherein the subject is identified as at risk for CHD if P1/R1 has a value in the first or second quartile of a population norm.

37. The system of claim 35, wherein the subject is identified as at risk for CHD if P1/R1 has a value ≤170 μmol$^2$/L$^2$.

38. The system of claim 29, wherein the at least one processor is configured to generate a report that visually and/or textually indicates whether the subject is at increased risk of CHD despite having elevated $HP_{VL}$.

39. The system of claim 29, wherein the at least one processor is configured to monitor whether there is a change in the at least one HDL risk interaction parameter over time to assess a change in CHD risk when $HP_{VL}$ remains above 1.84 μmol/L.

40. The system of claim 29, wherein the subject is mammalian, and wherein the at least one processor is configured to obtain NMR signal data of an in vitro blood plasma or serum sample of the subject to determine NMR derived concentration measurements, then provide a report indicating whether the subject is at risk of having and/or developing CHD based, in part, on the calculated at least one HDL interaction risk parameter.

* * * * *